(12) United States Patent
Borgqvist et al.

(10) Patent No.: US 12,714,773 B2
(45) Date of Patent: Aug. 25, 2026

(54) STATUS ASSESSMENT OF AN INDIVIDUAL UNDERGOING PERITONEAL DIALYSIS

(71) Applicant: GAMBRO LUNDIA AB, Lund (SE)

(72) Inventors: Per-Olof Borgqvist, Lund (SE); Carl Öberg, Lund (SE); Karin Bergling, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 581 days.

(21) Appl. No.: 18/024,445

(22) PCT Filed: Sep. 2, 2021

(86) PCT No.: PCT/EP2021/074288
§ 371 (c)(1),
(2) Date: Mar. 2, 2023

(87) PCT Pub. No.: WO2022/049208
PCT Pub. Date: Mar. 10, 2022

(65) Prior Publication Data

US 2023/0347034 A1 Nov. 2, 2023

(30) Foreign Application Priority Data

Sep. 4, 2020 (SE) .................................. 2051047-5

(51) Int. Cl.
*A61M 1/28* (2006.01)
*A61M 1/14* (2006.01)
(Continued)

(52) U.S. Cl.
CPC ............ *A61M 1/282* (2014.02); *A61M 1/154* (2022.05); *G16H 20/40* (2018.01); *G16H 50/30* (2018.01)

(58) Field of Classification Search
CPC ........ A61M 1/28; A61M 1/282; A61M 1/284; A61M 1/305; A61M 1/3403; A61M 1/341;
(Continued)

(56) References Cited

U.S. PATENT DOCUMENTS 2,623,139 A 12/1952 Weston
8,303,532 B2 11/2012 Hamada et al.
(Continued)

FOREIGN PATENT DOCUMENTS

EP 1623732 2/2006
EP 2623139 8/2013
(Continued)

OTHER PUBLICATIONS

International Search Report for International Application No. PCT/EP2021/074288 dated Jan. 11, 2022—5 pages.
(Continued)

*Primary Examiner* — Andrew Schechter
*Assistant Examiner* — Matthew W. Baca
(74) *Attorney, Agent, or Firm* — K&L Gates LLP

(57) ABSTRACT

A test method determines at least one status parameter of an individual undergoing peritoneal dialysis. The status parameter(s) may include a transport property of the peritoneum, a tonicity, or a residual volume. The test method includes receiving first data indicative of a flow rate as a function of time of a treatment fluid into and out of a peritoneal cavity during a test procedure, and second data comprising measured data samples representing a concentration of one or more solutes in the treatment fluid at time points during the test procedure. The test method also includes computing, based on the first data and by use of a transport model for a peritoneal membrane, estimated data samples representing the concentration of the one or more solutes in the treatment
(Continued)

fluid at the time points and determining the status parameter(s) as a function of the measured data samples and the estimated data samples.

20 Claims, 10 Drawing Sheets

(51) Int. Cl.
*G16H 20/40* (2018.01)
*G16H 50/30* (2018.01)

(58) Field of Classification Search
CPC .. A61M 1/3441; A61M 1/3465; A61M 1/154; A61M 1/1613; G16H 20/40; G16H 50/30; G16H 10/40
See application file for complete search history.

(56) References Cited

U.S. PATENT DOCUMENTS

| | | | | |
|---|---|---|---|---|
| 8,449,496 | B2 | 5/2013 | Hamada et al. | |
| 10,994,064 | B2 | 5/2021 | Gerber et al. | |
| 2015/0129499 | A1 | 5/2015 | Bene | |
| 2018/0043080 | A1 | 2/2018 | Gerber et al. | |
| 2019/0201607 | A1* | 7/2019 | Öberg | A61M 1/1565 |
| 2019/0351121 | A1* | 11/2019 | Akonur | A61M 1/1619 |
| 2020/0179583 | A1 | 6/2020 | Hobot et al. | |

FOREIGN PATENT DOCUMENTS

| | | | |
|---|---|---|---|
| EP | 2623139 A1 * | 8/2013 | A61M 1/282 |
| EP | 3281658 | 2/2018 | |
| JP | 2003275302 | 9/2003 | |
| JP | 2021076421 | 5/2021 | |
| JP | 2022070798 | 5/2022 | |
| WO | 2018031711 | 2/2018 | |
| WO | 2018041760 | 3/2018 | |

OTHER PUBLICATIONS

Written Opinion for Inlemational Application No. PCT/EP2021/074288 dated Jan. 11, 2022—11 pages

* cited by examiner

Kp0*
Kp1*
Kp2*
Kp2*
Kp3*
Kd0*
Kd1*
K (mS/cm)
CpNa (mM)
CpG (mM)
Vp (ml)
Time (min)
Δt1
Δt2

Kp0*
Kp1*
Kp2*
Kp22*
Kp23*
Kp24*
Kp25*
Kp26*
Kp3*
Kd0*
Kd1*
Kd12*
Kd13*
Kd14*
Kd15*
Kd16*
K (mS/cm)
CpNa (mM)
CpG (mM)
Vp (ml)
Time (min)

55
90
PET SIMULATION
92
D/D0
D/P 1.2
1
0.8
0.6
0.4
0.2
0
D/P
H
HA
LA
L
0
1
2
3
4
Time (h)

D/D0
LA
L
H
HA
Time (h)

15
14.5
14
13.5
13
12.5
12
Conductivity (ms/cm)
K1
K2
0
100
200
300
400
500
Time (min)

K1
K2
Time (min)

STATUS ASSESSMENT OF AN INDIVIDUAL UNDERGOING PERITONEAL DIALYSIS

PRIORITY CLAIM

This application is a national phase entry of PCT/EP2021/074288, filed Sep. 2, 2021, which claims priority to Swedish Patent Application No. 2051047-5, filed Sep. 4, 2020, the entire disclosures of which are incorporated herein by reference.

TECHNICAL FIELD

The present disclosure relates generally to peritoneal dialysis, and in particular to techniques for assessing the status of an individual undergoing peritoneal dialysis, for example the functionality of the individual's peritoneal membrane.

BACKGROUND ART

In the treatment of individuals suffering from acute or chronic renal insufficiency, dialysis therapy may be needed. One category of dialysis therapy is peritoneal dialysis (PD). In PD, a treatment fluid ("dialysate") is infused into the individual's peritoneal cavity. This cavity is lined by a peritoneal membrane ("peritoneum") which is highly vascularized. Substances are removed from the patient's blood mainly by diffusion across the peritoneum into the treatment fluid. Excess fluid (water) is also removed by osmosis induced by the treatment fluid being hypertonic.

There is considerable inter- and intra-patient variability in solute transport capacity and ultrafiltration capacity of the peritoneum. This variability makes it difficult to develop patient-optimized prescriptions for PD therapy. Moreover, continuous exposure to treatment fluids may lead to functional alterations of the peritoneum. Therefore, it is standard procedure to perform peritoneal testing to assess the functionality of the peritoneum. There are numerous options for peritoneal testing, including the peritoneal equilibration test (PET). There are many variants of PET, but the so-called Standard PET is currently most widely used and will be briefly described in the following.

The process may start with a long overnight dwell of 8-12 hours. When the patient arrives at the clinic on the morning of the PET, the overnight dwell is drained while the patient is sitting up for at least 20 minutes. To maximize the amount of effluent, the patient may lie down and roll from side to side at the end of the drain. For the PET, 2 L of a treatment fluid with a predefined concentration of an osmotic agent is infused over 10 minutes. Every 2 minutes, the patient rolls from side to side to mix the treatment fluid. Once the infusion is complete, 200 mL of treatment fluid is drained from the peritoneal cavity into a bag, and the drained treatment fluid is mixed by inverting the bag several times. Then, a 10-mL sample is obtained using aseptic technique, and the remaining treatment fluid is reinfused back into the patient. For the remainder of the 4-hour dwell, the patient is upright and ambulatory. At the 2-hour timepoint, another 10-mL sample is obtained and a blood sample is taken for serum measurements. After 4 hours of dwell, the patient is completely drained from an upright position for at least 20 minutes. The drain volume is measured by weighing before collecting a 10-mL sample of treatment fluid. Once the PET samples are collected, both the serum and treatment fluid samples are analyzed for concentrations of urea, creatinine and glucose. For urea and creatinine, a dialysate-to-plasma (D/P) ratio is calculated for each treatment fluid sample. For glucose, a D/DO ratio is calculated for each treatment fluid sample. From these equilibration ratios, the peritoneum is characterized into one of four transport types: High, High Average, Low Average, Low.

Apart from resulting in a coarse and rather non-informative characterization of the peritoneum, Standard PET is complicated and requires significant expenditure of time and resources, for example to run tests, perform laboratory analysis, interpret data, etc. Standard PET is performed by medical staff and is time-consuming for the patient, who needs spend at least half a day at a dedicated clinic or a hospital.

The prior art comprises EP2623139 which proposes a peritoneal functionality test which obviates the need for blood samples and laboratory analysis. The proposed test involves extracting a first sample of equilibrated treatment fluid from the peritoneal cavity and measuring its conductivity, draining the peritoneal cavity, infusing fresh treatment fluid into the peritoneal cavity, and extracting a second sample of equilibrated treatment fluid from the peritoneal cavity after a set dwell time, for example 1 hour, and measuring its conductivity. The difference in conductivity between the samples is used for classifying the transport through the peritoneum as defective, normal or optimal. While being considerable simpler than Standard PET, the proposed test results in an even coarser characterization of the functionality of the peritoneum. Further, the proposed test does not account for the residual volume, i.e. the amount of treatment fluid that may remain in the peritoneal cavity after draining. Variations in residual volume from patient to patient, or from test to test on the same patient, will have significant negative impact on the accuracy of the characterization.

SUMMARY

It is an objective to at least partly overcome one or more limitations of the prior art.

One objective is to provide a technique that enables a more detailed characterization of the functionality of the peritoneal membrane.

Another objective is to provide such a technique that obviates the need for serum samples.

Yet another objective is to provide a technique that is capable of quantifying the residual volume.

One or more of these objectives, as well as further objectives that may appear from the description below, are at least partly achieved by an arrangement for determining at least one status parameter of an individual undergoing peritoneal dialysis, a peritoneal dialysis arrangement, a method of determining at least one status parameter, a computer-readable medium, and a monitoring method according to the independent claims, embodiments thereof being defined by the dependent claims.

A first aspect is an arrangement for determining at least one status parameter of an individual undergoing peritoneal dialysis, said arrangement comprising:

- an input for receiving first data indicative of flow rate as a function of time of treatment fluid into and out of a peritoneal cavity, via a peritoneal access on the individual, during one or more fluid exchange cycles, wherein a respective fluid exchange cycle comprises a fill phase, a dwell phase and a drain phase, and second data comprising measured data samples representing concentration of one or more solutes in the treatment fluid in the peritoneal cavity at two or more time points during the one or more fluid exchange cycles;

a first computation module configured to compute, based on the first data and by use of a mathematical model of transport of water and solutes through a peritoneal membrane in the peritoneal cavity, estimated data samples representing the concentration of the one or more solutes in the treatment fluid in the peritoneal cavity at said two or more time points; and a second computation module configured to determine said at least one status parameter as a function of the measured data samples and the estimated data samples.

A second aspect is a peritoneal dialysis arrangement, comprising:

an extracorporeal fluid circuit that is connectable to a peritoneal access of an individual for conveying treatment fluid from/to a peritoneal cavity;

at least one sensor device, which is arranged in the extracorporeal fluid circuit and configured to provide data samples representative of concentration of one or more solutes in the treatment fluid;

a control apparatus configured to operate the extracorporeal fluid circuit and obtain the data samples from the sensor device; and an arrangement in accordance with the first aspect, which is connected to receive the first and second data from the control apparatus.

A third aspect is a method of determining at least one status parameter of an individual undergoing peritoneal dialysis, said method comprising:

obtaining first data indicative of flow rate as a function of time of treatment fluid into and out of a peritoneal cavity, via a peritoneal access on the individual, during one or more fluid exchange cycles, wherein a respective fluid exchange cycle comprises a fill phase, a dwell phase and a drain phase;

obtaining second data comprising measured data samples representing concentration of one or more solutes in the treatment fluid in the peritoneal cavity at two or more time points during the one or more fluid exchange cycles;

computing, based on the first data and by use of a mathematical model of transport of water and solutes through a peritoneal membrane in the peritoneal cavity, estimated data samples representing the concentration of the one or more solutes in the treatment fluid in the peritoneal cavity at said two or more time points; and determining said at least one status parameter as a function of the measured data samples and the estimated data samples.

A fourth aspect is a computer-readable medium comprising computer instructions which, when executed by one or more processors, cause the one or more processors to perform the method of the third aspect.

A fifth aspect is a monitoring method, comprising:

operating the arrangement of the first aspect to determine the at least one status parameter; and evaluating the at least one status parameter for detection of a potential failure of the peritoneal membrane.

These aspects take a fundamentally different approach compared to prior art techniques. The measured concentration of one or more solutes, or an equivalent property such as electrical conductivity, in the peritoneal fluid in the peritoneal cavity is used as reference data for determining one or more status parameters that affect the concentration. The respective status parameter is a property of the individual that is presumed to have a known time dependence during the fluid exchange cycle(s) and that affects the amount of treatment fluid in the peritoneal cavity and/or the concentration of one or more solutes in the treatment fluid in the peritoneal cavity. Specifically, the aspects are based on the insight that since the concentration of solutes is affected by the status parameter(s), it is possible to determine the status parameter(s) by conducting a simulation of the concentration of solutes in the treatment fluid in the peritoneal cavity and comparing the resulting ("estimated") concentration of one or more solutes (or electrical conductivity) to the measured concentration (or electrical conductivity). When the estimated and measured concentrations (or conductivities) substantially match, the value of the respective status parameter used in the simulation will be close to the actual value. To simulate the concentration or conductivity in the treatment fluid in the peritoneal cavity, a mathematical model of the transport of solutes and water through the peritoneal membrane is used. The simulation is performed by use of first data that is indicative of the flow rate as a function of time of treatment fluid into and out of the peritoneal cavity via the peritoneal access during the fluid exchange cycle(s). The skilled person understands that the simulation may use further input data, such as the composition and/or conductivity of the treatment fluid that is infused into the peritoneal cavity during the fill phase(s), various properties of one or more solutes in the treatment fluid, initial values of the status parameter(s), etc. For reasonable accuracy in the determined status parameter(s), the reference data should include at least two measured data samples, which are thus obtained at different time points during the fluid exchange cycle(s). If data samples are measured at a larger number of time points, the accuracy of a status parameter may be increased and/or additional status parameters may be determined. The time points may be selected differently depending on the status parameter(s) to be determined. Examples of status parameters include a transport property of the peritoneal membrane, a volume of treatment fluid in the peritoneal cavity at a specified time point (for example, the residual volume), or a tonicity parameter of the individual.

It is thus realized that the foregoing aspects, by determining the status parameter(s), enable a more detailed characterization or quantification of the functionality of the peritoneal membrane. Furthermore, this is achieved by the simple procedure of measuring concentration or conductivity in the treatment fluid in the peritoneal cavity, for example by extracting a fluid sample from the peritoneal cavity, and does not require serum samples to be taken and analyzed. In some embodiments, at least one of the measured data samples may be conveniently obtained for a drain phase. Still further, the foregoing aspects enable the status parameter(s) to be determined during a regular PD treatment session. The treatment efficiency of such a PD treatment session will only be moderately impacted by the possible extraction of a fluid sample from the peritoneal cavity for concentration or conductivity measurement at one or more time points during the fluid exchange cycle(s).

Still other objectives, aspects and technical effects, as well as embodiments, features and advantages may appear from the following detailed description, from the attached claims as well as from the drawings. It may be noted that any embodiment of the first aspect, as found herein, may be adapted and implemented as an embodiment of the second to fifth aspects.

BRIEF DESCRIPTION OF THE DRAWINGS

Embodiments will now be described in more detail with reference to the accompanying and schematic drawings.

DETAILED DESCRIPTION OF EXAMPLE EMBODIMENTS

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments.

As used herein, the terms "multiple", "plural" and "plurality" are intended to imply provision of two or more elements, whereas the term a "set" of elements is intended to imply a provision of one or more elements. The term "and/or" includes any and all combinations of one or more of the associated listed elements.

A parameter or variable within square brackets ([ ]) designates a sequence of values of the parameter or variable. Further, an asterisk (*) on a parameter or variable designates that the value of the parameter or variable has been obtained by measurement.

It will furthermore be understood that although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure.

Well-known functions or constructions may not be described in detail for brevity and/or clarity. Unless otherwise defined, all terms (including technical and scientific terms) used herein have the same meaning as commonly understood by one of ordinary skill in the art to which this disclosure belongs.

Like reference signs refer to like elements throughout.

Figure 1:
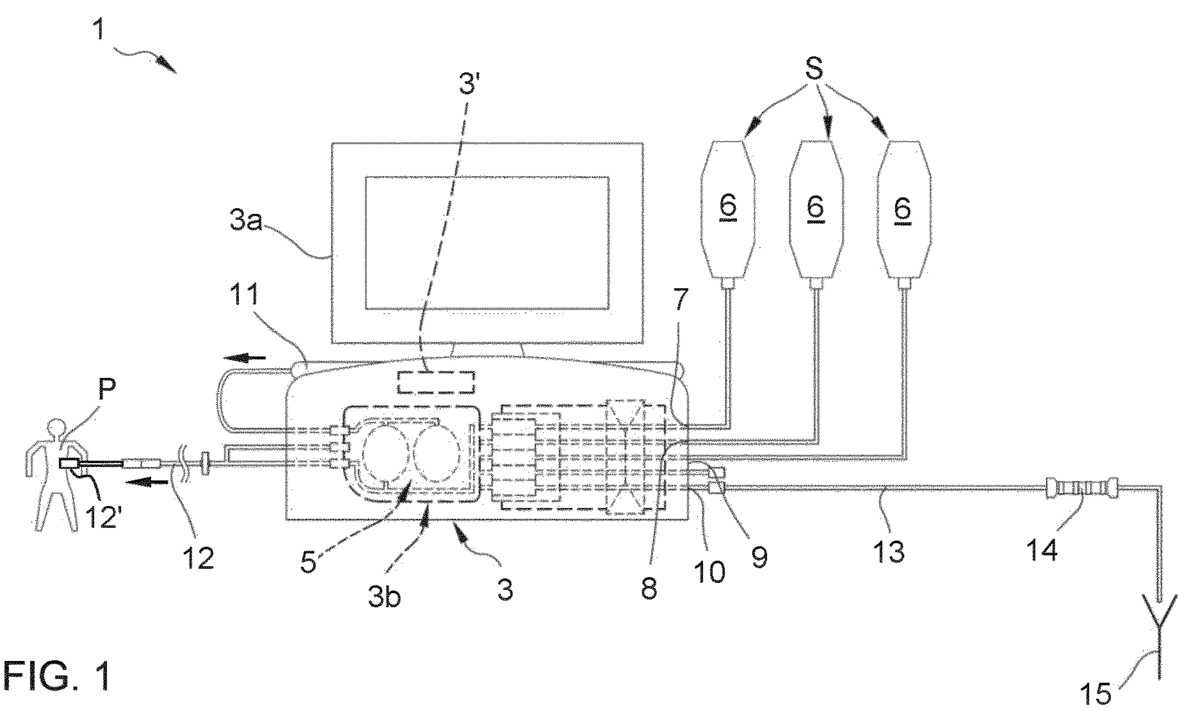
FIG. 1 illustrates an example arrangement for automated peritoneal dialysis (APD).

FIG. 1 is a schematic view of an example arrangement 1 for peritoneal dialysis treatment. The arrangement (or system) 1 is generally intended for on-site treatment of a patient P with proper treatment fluid(s). Specifically, the PD arrangement 1 is designed for treating patients suffering of renal insufficiency, particularly with an automated peritoneal dialysis (APD) cycler 3.

The APD cycler 3 comprises a peritoneal dialysis (PD) unit 3*a* and a corresponding disposable unit 3*b*, sometimes referred to as a "disposable line set". The PD unit 3*a* includes a control system 3' connected to actuators 5 forming a pumping mechanism for moving fluid in the hydraulic circuit of the disposable unit 3*b*.

The disposable unit 3*b* is connectable on the PD unit 3*a*, for engagement by the pumping mechanism 5 in the PD unit 3*a*. A patient line 12 is included in or connected to the disposable unit 3*b* and is configured for connection to a catheter or other access device 12' implanted in the patient P. The access device 12' is referred to as "access" in the following.

The PD arrangement 1 includes a source S of treatment fluid, in the example of FIG. 1 comprising three containers 6, which are connected through a respective feeding line to corresponding treatment ports 7, 8, 9 of the disposable unit 3*b*. The number of containers 6 in the source S may differ depending on the treatment fluids to be infused in the peritoneal cavity (PC) during the course of the PD treatment. For example, different containers may hold treatment fluid of different composition. In an alternative, the source S comprises an apparatus for on-line preparation of treatment fluid, for example by mixing purified water and one or more concentrates.

The treatment fluid may comprise at least one osmotic agent. As is well-known in the art, the osmotic concentration of the treatment fluid relative to the blood determines to what extent fluids are exchanged between the treatment fluid and the blood. A high osmotic concentration in the treatment fluid creates a high gradient. In any of the embodiments described herein, the osmotic agent may be, or include, glucose (or polyglucose), L-carnitine, glycerol, icodextrin, or any other suitable agents. Alternative osmotic agents may be fructose, sorbitol, mannitol and xylitol. It is noted that glucose is also sometimes named as dextrose in the PD field. The term glucose is herewith intended to comprise dextrose.

In the illustrated example of FIG. 1, the disposable unit 3*b* further includes or is connected to a delivery container 11, sometimes referred to as a "heating bag", which is configured to receive fresh treatment fluid from the source S. The delivery container 11 is arranged on a heater (not shown) of the PD unit 3*a*. The heater is operated to adjust the temperature of the treatment fluid to a predefined temperature before it is pumped into the PC of the patient P. The disposable unit 3*b* further includes or is connected to a drain line 13, which is arranged to receive spent treatment fluid through a drain port 10 on the disposable unit 3*b*. The drain line 13 extends to a drain 15. In an alternative, not shown, the drain line 13 may extend to a receptable for spent treatment fluid.

The PD arrangement 1 further includes at least one sensor 14 for detecting a property of the fluid flowing in the disposable unit 3*b*, or in a line or container fluidly connected with the disposable unit 3*b*, for example the drain line 13. In some embodiments, the sensor 14 is a conductivity sensor for measuring the electrical conductivity of a passing fluid. In some embodiments, the sensor 14 is a concentration sensor for measuring a concentration of one or more substances in a passing fluid. The sensor 14 need not be installed in the drain line 14 but could be installed anywhere in the disposable unit or in the above-mentioned source S for on-line generation of treatment fluid. Further, the PD arrangement 1 may comprise more than one such sensor 14. In some embodiments, the PD arrangement 1 comprises one such sensor 14 arranged to sense a property of drained treatment fluid from the PC of the patient. In some embodiments, the PD arrangement comprises another such sensor 14 arranged to sense a property of fresh treatment fluid intended to be infused into the PC of the patient. In some embodiments, the sensor 14 that is arranged to sense a property of drained treatment fluid is also arranged to sense a property of the fresh treatment fluid, by pumping a sample of the fresh treatment fluid to the sensor 14.

Although not shown in FIG. 1, the PD arrangement 1 may comprise further sensors for detecting other properties of the fluid, for example one or more flow rate sensors for measuring the flow rate of treatment fluid into and out of the PC of the patient P, a temperature sensor for measuring the temperature of the treatment fluid, etc. The flow rate sensor(s) may have any location in the PD arrangement and may, for example, determine fluid flow rate by weight change, volumetric throughput or dead reckoning of pump strokes. It should be understood, however, that the flow rates used for the calculating need not be measured by one or more flow meters but may be given by set values for the PD arrangement 1 (cf. test regimen data 54A in FIG. 5A).

The PD arrangement 1 is operable, by the control unit 3', to perform a PD treatment comprising one or more fluid exchange cycles. The respective exchange cycle comprises a sequence of a fill phase, a dwell phase and a drain phase. In the fill phase, the PD arrangement 1 is operated to pump fresh treatment fluid from the delivery container 11, via the patient line 12 and the access 12', to the PC of the patient P. In the dwell phase, the treatment fluid resides in the PC. In the drain phase, the PD arrangement 1 is operated to pump spent treatment fluid from the PC, via the access 12' and the lines 12, 13, to the drain 15. The spent treatment fluid is also known as "effluent" in the art.

Figure 2:
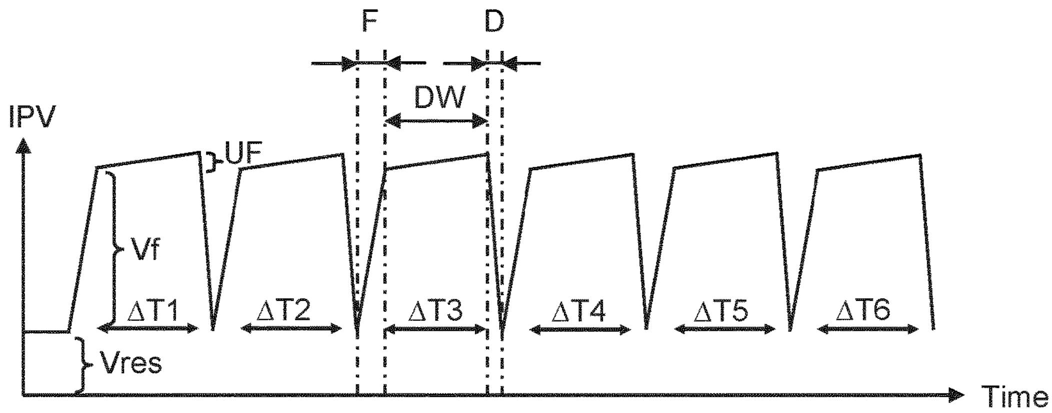
FIG. 2 is an example plot of intraperitoneal volume versus time during a sequence of fluid exchange cycles in APD therapy.

FIG. 2 schematically represents a PD treatment in terms of the intraperitoneal volume, IPV, as a function of time. IPV designates the amount of treatment fluid that resides in the PC and is also denoted Vp herein. The illustrated PD treatment comprises six consecutive exchange cycles. The fill, dwell and drain phases are designated F, DW and D and are indicated for the third exchange cycle. The durations of the dwell phases, which may differ between the exchange cycles, are indicated by ΔT1-ΔT6. In the illustrated example, the patient has a residual volume in the PC at the start, denoted Vres. In the first exchange cycle, an amount Vf of treatment fluid is infused into the PC. During the phases F, DW and D, the amount of treatment fluid in the PC is increased by transport of fluid from the patient's blood to the PC via the peritoneal membrane, known as ultrafiltration (UF). Depending on the osmotic pressure gradient both positive and negative UF is possible. For illustration purposes, UF is only indicated for the dwell phase DW in FIG. 2. During the drain phase, spent treatment fluid is extracted from the PC, leaving a residual volume. This residual volume may differ from the residual volume at the onset of the PD treatment and may also differ from drain to drain.

In the example of FIG. 2, the PD treatment is completed with a drain phase, and the next PD treatment is started with a fill phase. However, although not shown in FIG. 2, it is common that the PD treatment is completed by a fill phase that leaves treatment fluid in the PC. The patient will then disconnect from the PD arrangement 1 and may carry the treatment fluid in the PC until the next treatment session or perform a manual drain after a selected dwell time. APD is commonly performed in the night while the patient sleeps, allowing the patient to move freely during the day. From this follows that the PD treatment may start by a drain phase ("initial drain"), which is not shown in FIG. 2, which leaves the residual volume, Vres.

Figure 3:
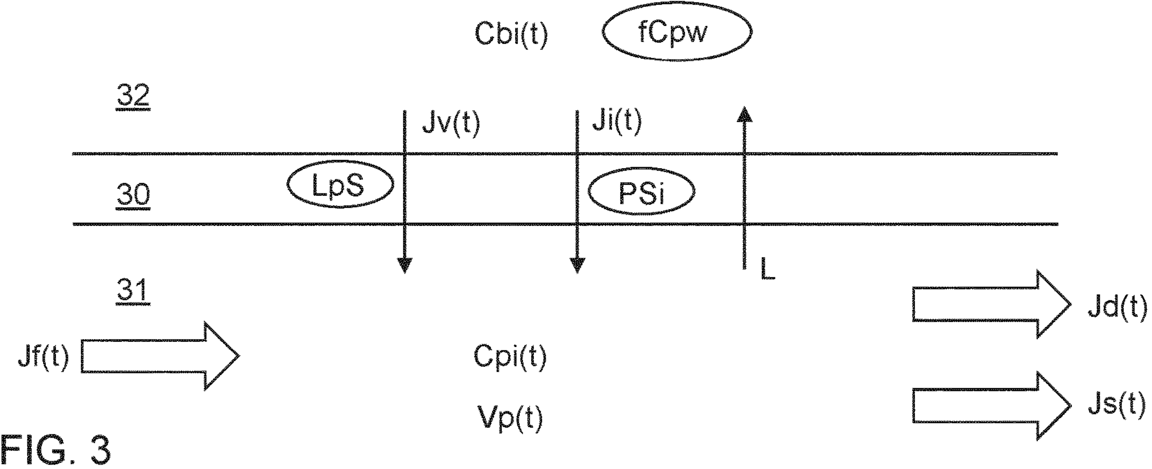
FIG. 3 illustrates transport processes affecting the concentration of solutes and the amount of treatment fluid in a peritoneal cavity.

FIG. 3 is a schematic view of a peritoneal membrane ("peritoneum") 30 that separates the PC 31 from the blood side 32 of the patient. In FIG. 3, the concentration of a respective solute (i) on the blood side 32 as a function of time is denoted Cbi(t), the intraperitoneal volume as a function of time is denoted Vp(t), and the concentration of the respective solute (i) in the treatment fluid as a function of time is denoted Cpi(t). The solutes may include, without limitation, sodium, potassium, calcium, magnesium, lactate, phosphate, albumin, bicarbonate, urea, creatinine, chloride, etc. The solutes may also include an osmotic agent, for example according to any of the examples hereinabove. In the following examples, the osmotic agent is assumed to be glucose. FIG. 3 also depicts processes that may affect Vp(t) and Cpi(t). The processes comprise fluid flows through the access 12', including a flow of treatment fluid into the PC 31 via the access 12' during the fill phase(s), denoted Jf(t), a flow of treatment fluid out of the PC 31 via the access 12' during the drain phase(s), denoted Jd(t), and a loss of treatment fluid from the PC 31 when fluid samples (see below) are taken of the treatment fluid in the PC 31 via the access 12', denoted Js(t). The processes further comprise fluid flows through the peritoneum 30, including a total fluid flow, denoted Jv(t), a solute flow of the respective solute, denoted Ji(t), and a lymphatic flow, denoted L. It should be understood that the respective substance may move in either direction across the membrane 30 and that the arrows in FIG. 3 merely indicate a direction corresponding to a positive sign for the respective flow.

The peritoneum 30 may be characterized by its transport properties. FIG. 3 indicate two such transport properties, LpS and PS. The property LpS is a hydraulic conductance of the membrane 30 and is also known as fluid permeability or ultrafiltration coefficient. The property LpS may, for example, be expressed in mL/min/mmHg. The property PS is a permeability-surface area product, which is also known as mass transfer area coefficient or diffusive mass transfer area coefficient and which represents the flow of a solute (molecule) through the membrane 30. The property PS may, for example, be expressed in mL/min. The property PS generally differs between solutes and is therefore denoted PSi herein. In some embodiments, it is assumed that there is a predefined relation between the PSi for all solutes, so that the PSi for any solute may be computed if the PSi for one solute is known. This assumption will facilitate the calculations, since determining PSi for a plurality of different solutes may be reduced to determining a scaling factor, fPS, that scales a generic set of PS values for the different solutes, PSiG, according to: PSi=*f*PS·PSiG, where PSiG is the generic PS value for solute i. The generic set represents the above-mentioned predefined relation and may be seen to include PS values representative of a "generic patient". When fPS has been determined, any PSi may be determined by scaling the corresponding PSiG with fPS.

FIG. 3 also indicates a further scaling factor, fCpw, which is representative of the tonicity of the patient and may represent the patient's deviation from an isotonic status. In some embodiments, to avoid the need for taking serum samples of the patient, the blood concentrations Cbi(t) of the solutes may be set to fixed (time-invariant) values for a standard (nominal) patient. To account for the fact that the tonicity may differ between patients, fCpw may be applied to scale the nominal blood concentration values. Thus, the scaling factor fCpw may be seen to account for the patient's actual plasma water fraction.

Embodiments to be described provide a technique of estimating one or more status parameters of the patient P by use of a kinetic model of the concentrations of solutes in the treatment fluid in the PC 31. The kinetic model depends on the one or more status parameters and accounts for the time dynamics of the flows of treatment fluid represented by Jf(t), Jd(t) and Js(t) in FIG. 3, as well as the time dynamics of the fluid flow Jv(t) and the solute flows Ji(t) through the membrane 30. Such embodiments rely on the insight that it is possible to estimate the status parameter(s) by comparing estimated data samples, which are representative of the concentration of one or more solutes in the treatment fluid estimated by the kinetic model at a set of time points, with measured data samples, which are representative of the actual concentration of the solute(s) measured at the set of time points.

It may be noted that "representative of concentration" in this context includes any and all equivalent properties. In one example, the data samples comprise concentration values of at least one of the solutes in the treatment fluid, for example the osmotic agent or sodium. In another example, the data samples comprise conductivity values measured by one or more conductivity sensors (cf. 14 in FIG. 1). For simplicity, the following description presumes that the data samples are conductivity values. Corresponding embodiments based on concentration values are readily apparent to the person skilled in the art.

Figures 4A, 4B, 4C, 5A:
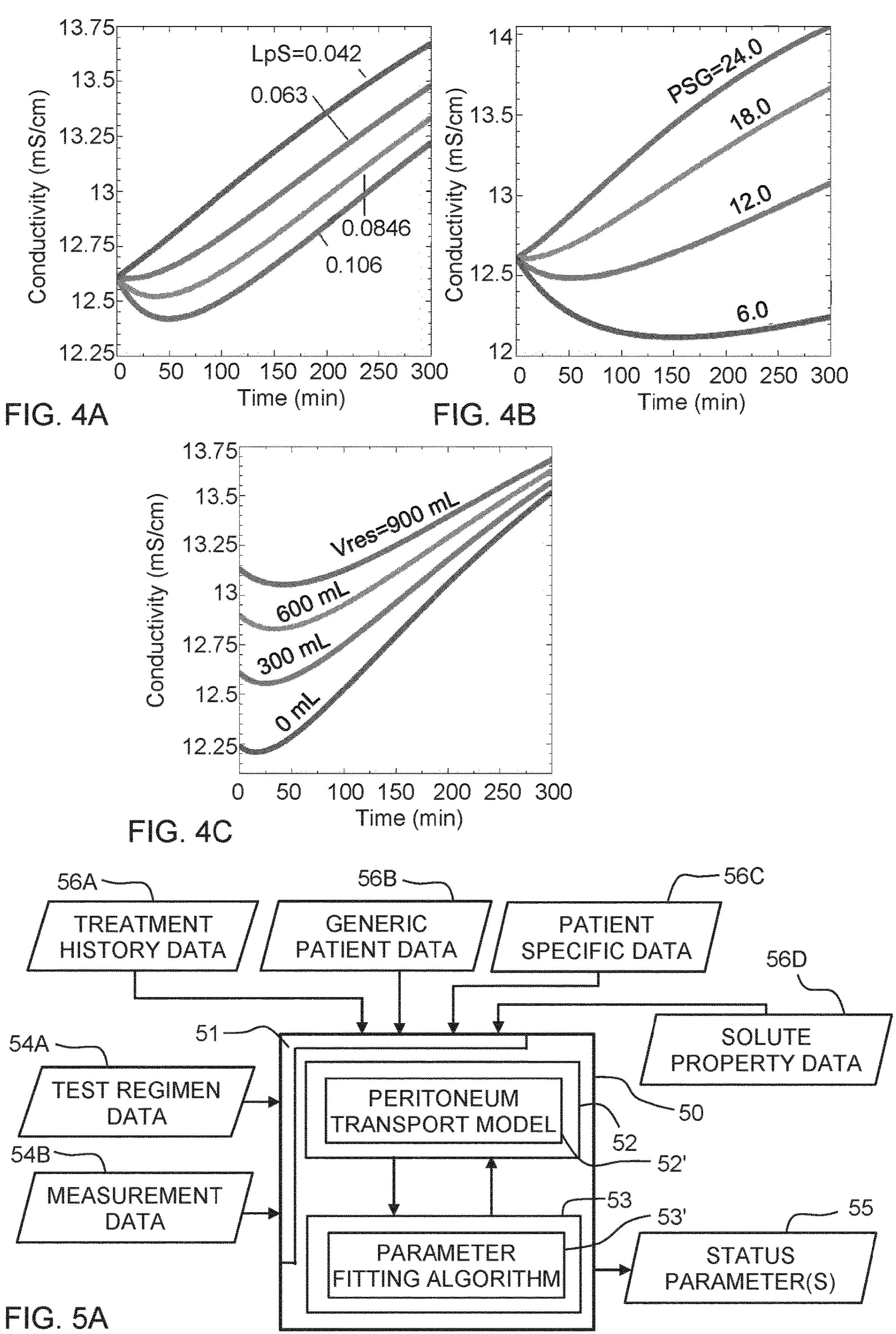
FIGS. 4A-4C are plots of treatment fluid conductivity in a peritoneal cavity as a function of time for different values of the ultrafiltration coefficient, the permeability surface area product for glucose, and the residual volume, respectively.
FIGS. 5A-5B are block diagrams of example computation arrangements for determining status parameter(s) of a PD patient.

The utility of the proposed embodiments is illustrated in FIGS. 4A-4C which are simulated graphs of the conductivity of a treatment fluid in a PC over a time period of 300 minutes. FIG. 4A shows conductivity for different values of LpS and with a fixed PSG of 15.27 mL/min, where PSG is the PS value for glucose. FIG. 4B shows conductivity for different values of PSG and with a fixed LpS of 0.074 mL/min/mmHg. FIG. 4C shows conductivity for different values of the residual volume, Vres, with fixed values of LpS and PSG. As understood from FIGS. 4A-4C, the transport properties of the peritoneum and the residual volume of treatment fluid in the PC each has a large impact on the resulting conductivity of the treatment fluid (and the concentration of various solutes therein) over time. A similar impact may be demonstrated for the scaling factor fCpw.

In some embodiments, the kinetic model is based on the well-known Three-Pore Model (TPM) of the peritoneum. The TPM is a transport model that assumes that the blood vessel wall of the peritoneum has three types of pores with different pore radii, enabling passive transport of molecules with different size properties. The smallest pore type, called Aquaporine-1 (AQP-1), is a water selective pore-structure. The AQP-1 pore enables passive transport of water, i.e. UF driven by osmotic force. A medium pore type permits transport of fluid and smaller solutes. The majority of protein transport over the membrane is enabled by a large pore type. Examples of TPM are found in WO2018/041760 and the article "Optimizing Automated Peritoneal Dialysis Using an Extended 3-pore Model", by C. Öberg and B. Rippe, published in Kidney Int Rep., 2(5):943-951 (2017), which are both incorporated herein in their entirety by reference.

Equations representing the processes in FIG. 3 are presented in detail in Appendix A. While these equations are based on TPM, other kinetic models may be used instead, for example the Two-Pore Model, the Dual Barrier Membrane Model, or the Distributed Model, as readily understood by the skilled person.

Equations 1-4 in Appendix A may be generalized into basic time-dependent governing functions for fluid flow through the peritoneum, $J_v(t)$, for the flow of solute i through the peritoneum, $J_i(t)$, for the temporal change in intraperitoneal volume, $dV_p/dt$, and for the temporal change in concentration of solute i the treatment fluid in the PC, $dC_{pi}/dt$:

$$J_v(t) = f1(LpS, V_p(t), C_{p1 \ldots N}(t))$$

$$J_i(t) = f2(LpS, V_p(t), C_{p1 \ldots N}(t), PS_{1 \ldots N}, J_v(t))$$

-continued $$\frac{dV_p(t)}{dt} = f3(J_v(t), J_f(t), J_d(t), J_s(t))$$

$$\frac{dC_{pi}(t)}{dt} = f4(J_i(t), J_v(t), J_f(t), V_p(t), C_{pi}(t))$$

where $C_{p1 \ldots N}(t)$ designates the ensemble of concentration values for all included solutes at time t, and $PS_{1 \ldots N}$ designates the ensemble of PS values for all included solutes.

As seen, and understood from Appendix A, the governing functions have a complex and intermixed dependence on time-dependent variables shown in FIG. 3, as well as on the transport properties, LpS and PSi. The governing functions ƒ1, ƒ2, β, ƒ4 may be combined to define a peritoneum transport model, as will be exemplified in the following with reference to FIGS. 5A-5C.

It may be noted that the above-mentioned scale factor, fCpw, is included in Cbi (cf. FIG. 3), which is used for calculation of both $J_v(t)$ and $J_i(t)$ (cf. Eq. 2 and Eq. 4 in Appendix A). Thus, the governing functions ƒ1 and ƒ2 will also depend on fCpw, if used.

It may also be noted from Appendix A that function ƒ2 may operate on $PS_{i,m}$, which designates a pore-type-specific value. In some embodiments, the PS values for large pores ($PS_{i,3}$) are set to generic values, for example given by the above-mentioned generic set, and the scaling factor fPS may be applied only to the PS values for small pores ($PS_{i,2}$). The PS value for a specific solute may then be computed by scaling the sum of the corresponding generic PS values for small and large pores by the scaling factor fPS. This simplification has been found to have little impact on the accuracy of the results. However, in other embodiments, the scaling factor fPS may be applied to the PS values for both small pores ($PS_{i,2}$) and large pores ($PS_{i,3}$). As a further simplification, the PS value for a specific solute may be computed by scaling the corresponding PSiG for small pores by the scaling factor fPS and thus omitting the contribution from large pores. This further simplification is at least applicable to small solutes, for example glucose or sodium, for which the contribution to the PSi from large pores may be effectively negligible.

FIG. 5A is a block diagram of an example peritoneum test arrangement 50 ("PT arrangement") for determining one or more status parameters of an individual based on measurements conducted during a test procedure performed by a PD arrangement 1, for example as shown in FIG. 1 in relation to patient P. The test procedure comprises one or more fluid exchange cycles. The PT arrangement 50 comprises an input 51, which may include any type of hardware and/or software structure that is configured to receive input data in any format. For example, the input 51 may be an interface configured to receive signals from one or more sensors (cf. 14 in FIG. 1), from a control unit (cf. 3' in FIG. 1), from a storage memory, or from an input unit such as a keyboard, touchpad, touch screen, computer mouse, etc. In the illustrated example, the PT arrangement 50 is configured to receive, via the input 51, test regimen data 54A, measurement data 54B, treatment history data 56A, generic patient data 56B, patient specific data 56C, and solute property data 56D. The PT arrangement 50 further comprises a first computation module 52 and a second computation module 53, which are cooperatively operated to determine one or more status parameters 55, which may be output for presentation, storage, further processing, etc. The first computation module 52 defines or comprises a peritoneum transport model (PTM) 52', which is a mathematical model of the transport of water and solutes through the peritoneum in the PC of the individual and which also accounts for the transport of treatment fluid into and out of the PC through the access 12'. For example, the PTM 52' may be an implementation of the governing functions ƒ1-ƒ4. The first computation module 52 is configured to operate the PTM 52' on at least part of the input data that is received via the input 51 to generate estimated data samples corresponding to the measurement data 54B. The second computation module 53 defines or comprises a parameter fitting algorithm (PFA) 53', which is configured to operate on the estimated data samples from the first computation module 52 and the measurement data 54B, to determine candidate property data of the individual. The candidate property data comprises one or more parameters that are processed by the PTM 52' for generation of the estimated data samples. The first and second computation modules 51, 52 are configured to alternately generate the estimated data samples and the candidate property data until the PFA 53' finds that the candidate property data fulfils a convergence criterion, or a time limit expires. The PT arrangement 50 then generates the status parameter(s) 55 based on the candidate property data. The PFA 53' may be any algorithm capable of solving non-linear optimization problems and enabling fitting of experimental data to simulated data. Such algorithms include any non-linear programming (NLP) algorithm such as algorithms for least-squares minimization. The results presented herein has been generated by use of the standard function Lsqnonlin in MATLAB.

Looking more in detail at the input data presented in FIG. 5A, the test regimen data 54A represents the flow rate of treatment fluid, as a function of time, into and out of the PC, via the access 12', during the test procedure. In the notation of FIG. 3, the test regimen data 54A is thus indicative of Jf(t), Jd(t) and Js(t), as well as start and end times of the test procedure. The test regimen data may also be indicative of the composition of the fresh treatment fluid (cf. in Eq. 3 in Appendix A). It is to be noted that the composition of the fresh treatment fluid may differ between fluid exchange cycles.

In the following examples, the measurement data 54B is representative of measured electrical conductivity of the treatment fluid inside the PC at a set of time points during the one or more fluid exchange cycles. The measurement data 54B may also identify the set of time points, if not predefined. In the example of FIG. 1, the conductivity may be measured by the sensor 14, as will be described in further detail below with reference to FIG. 7.

The treatment history data 56A may include test regimen data for one or more fluid exchange cycles performed on the individual in a preceding time period, for example within 12-48 hours of the test procedure.

The generic patient data 56B may include the above-mentioned generic set of PSi values, as well as generic values of plasma concentrations of solutes (cf. Cbi in FIG. 3). In some embodiments, all solutes that are expected to be present in blood or treatment fluid in a concentration of at least about 0.5 mmol/L are included in the PTM 52' and thus also in the generic patient data 56B. The generic values may be given as population averaged values. It is understood that the generic patient data 56B may also include other parameter values used by the PTM 52', such as am (see Appendix A).

The patient specific data 56C may include any known or estimated property of the patient of relevance to the calculations by the PT arrangement 50. For example, the patient specific data may include concentrations of one or more solutes in the patient's blood, or a previously determined value of Vres, LpS, PSi or fCpw (cf. FIG. 3). It is realized that the provision of patient specific data 56C may reduce the complexity and/or increase the accuracy of the calculations by the PT arrangement 50.

The solute property data 56D may include any known property data of the solutes that are included in the governing functions used by the PTM 52'. In the example of Appendix A, the solute property data 56D may include one or more of osmotic coefficients ($\varphi_i$), charges of the solutes ($z_i$), etc.

The input data shown in FIG. 5A and described above is not intended to be limiting and is only provided as an example. It is conceivable that additional input data is used and/or that one or more of the data items 56A-56D are omitted. For example, the patient specific data 56C may not be available. In another example, all or part of the solute property data 56D may be integrated into the PTM 52'. Further, the treatment history data 56A may be omitted altogether.

Figure 5B:
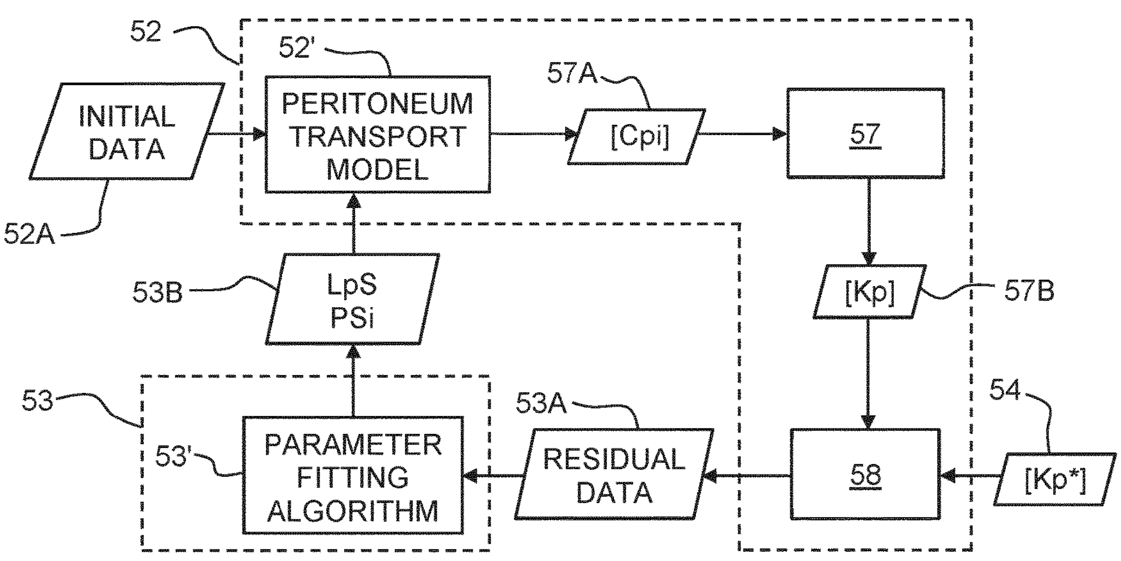

FIG. 5B is a block diagram of a more detailed example of the first and second computation modules 52, 53 in the PT arrangement 50 (FIG. 5A). In FIG. 5B, the PT arrangement 50 is configured to receive input data 54 comprising a set of data samples, [Kp*], that have been measured to represent the conductivity of the treatment fluid in the PC at the above-mentioned set of time points. The input data 54 may be part of the measurement data 54A of FIG. 5A. The PTM 52' is configured to receive an initial dataset 52A comprising initial values of variables in the governing functions and to operate on the initial dataset 52A to generate a dataset 57A comprising a sequence of estimated values for the concentrations of the solutes, [Cpi], in the treatment fluid within the PC. The estimated values are generated for time points that at least approximately match the set of time points of [Kp*]. In the illustrated example, the PT arrangement 50 further comprises a conversion module 57, which is configured to convert the estimated concentrations [Cpi] of the solutes at each time point into a corresponding estimated conductivity [Kp] the treatment fluid. The conversion module 57 may be configured to aggregate the conductivity contribution of all charged solutes, given their concentrations, while possibly also accounting for the effect of uncharged solutes, such as glucose and urea (if present). The conversion module 57 may thus be configured in accordance with well-known and standard equations, for example as described US2012/0018379 and WO2016/188950, which are incorporated herein by reference. The output data 57B of the conversion module 57, comprising [Kp], is received by a subtraction module 58, which is configured to compute the difference between corresponding values in [Kp] and [Kp*], i.e. between estimated conductivity values and measured conductivity values at the set of time points. The result is a sequence of difference values for the set of time points, represented as residual data 53A in FIG. 5B. The PFA 53' is configured to operate on the residual data 53A to generate the above-mentioned candidate property data 53B, exemplified as LpS and PSi in FIG. 5B. The PTM 52' is configured to then operate on the candidate property data 53B, and possibly on at least part of the initial dataset 52A, to generate a new dataset 57A, comprising updated [Cpi]. As understood from the foregoing, the calculations and flow of data may continue until the PFA 53' finds that a convergence criterion is fulfilled, for example that the residual data 53A is small enough. The PT arrangement in FIG. 5B may be seen to represent a feedback control system in which the first computation module 52 corresponds to the system to be controlled, the input data 54 corresponds to set values, the output data 57B corresponds to actual values, and the PFA 53' corresponds to the controller.

In some embodiments, the candidate property data 53B is presumed to be time invariant (constant) during the test procedure, which may facilitate the calculations. However, it is also possible for one or more parameters in the candidate property data 53B to be time varying by including a predefined time dependence for the respective parameter. For example, it previously known to model a declining time dependence of PSi and/or LpS during PD, for example as described in the article "Diffusive Mass Transfer Coefficients Are Not Constant During a Single Exchange In Continuous Ambulatory Peritoneal Dialysis", by Waniewski et al, published in ASAIO J 1996; 42:M518-523, which is incorporated herein in its entirety by reference.

It is also to be understood that the candidate property data 53B may include any unknown property that is included in the governing functions of the PTM 52'. In the example of FIG. 5B, it is presumed that fCpw is known, and LpS and PSi are fitted by the PFA 53'. In another example, the candidate property data 53B includes fCpw, LpS and PSi. In other examples, only one of LpS, PSi and fCpw is fitted by PFA 53', while the others are set to fixed and known values.

In some embodiments, as mentioned above, PSi may be represented by the scaling factor fPS. Thus, the scaling factor fPS may be fitted by PFA 53' or be set to a fixed and known value.

The conversion module 57 and the subtraction module 58 need not be included in the first computation module 52, as shown in FIG. 5B, but one or both of the modules 57, 58 may instead be included in the second computation module 53 or in a third computation module.

Figure 5C:
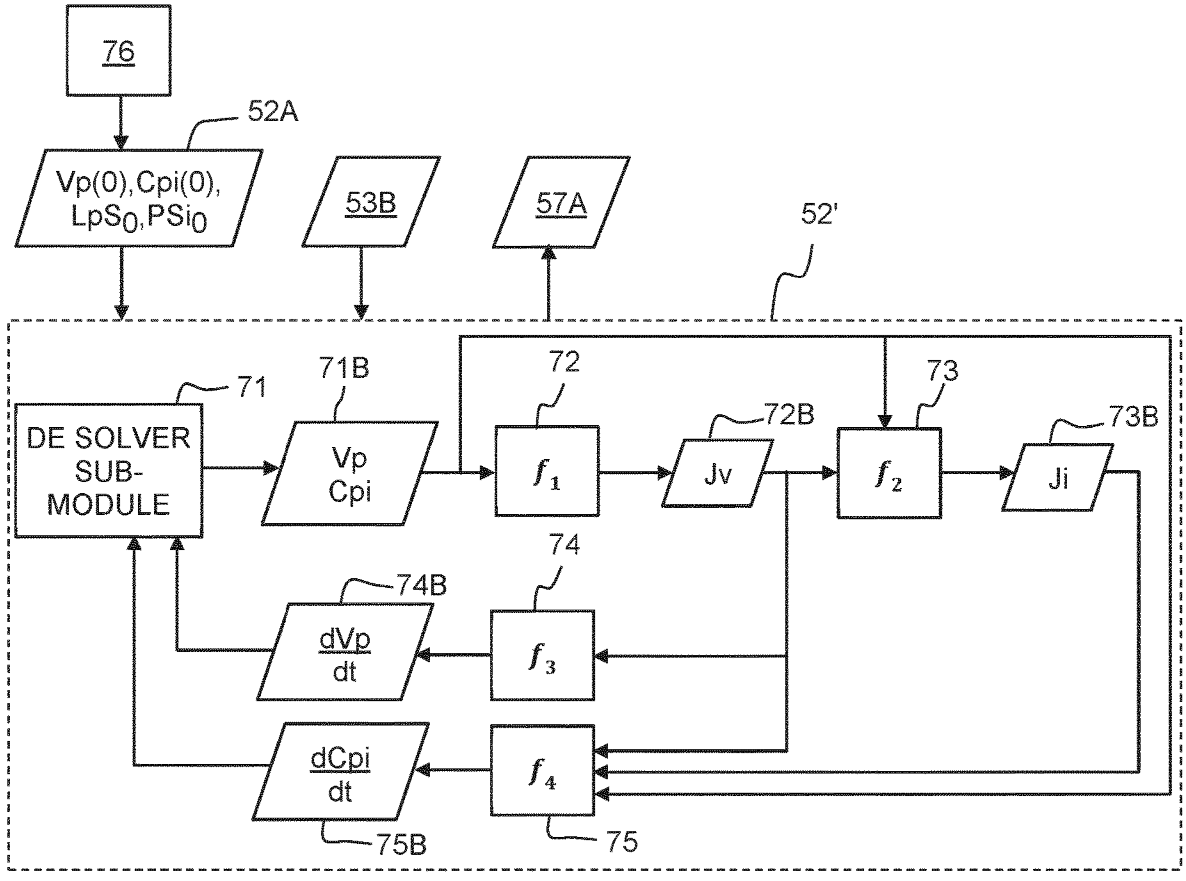
FIG. 5C is a block diagram of an example implementation of a peritoneum transport model in a computation arrangement.

FIG. 5C is a block diagram of a more detailed example of the PTM 52'. Generally, the PTM 52' is configured to implement the governing functions $f1$-$f4$. In the illustrated example, the PTM 52' comprises a differential equation solver sub-module (DES) 71 which is configured to operate on a value of the derivative ("temporal change") of a variable at one or more previous time steps to generate the value of variable at a current time step. For example, the DES sub-module 71 may implement any known regression method for obtaining numerical solutions to differential equations, such as a linear multistep method, a Runge-Kutta method, or a general linear method (GLM). The results presented herein have been generated by implementing the PTM 52' on a conventional ODE (Ordinary Differential Equation) solver, specifically the ode45 function in MATLAB.

In the illustrated example, the PTM 52' is configured to generate a time series of values of the intraperitoneal volume, Vp, and a corresponding time series of values of the concentrations of solutes, Cpi, in the treatment fluid in the PC. To this end, the PTM 52' further comprises governing sub-modules 72-75, which implement a respective governing function $f1$-$f4$. During operation, the DES sub-module 71 generates a dataset 71B comprising Vp, Cpi for the current time step based on datasets 74B, 75B comprising the derivatives of Vp and Cpi for the preceding time step. The governing sub-module 72 operates on Vp, Cpi for the current time step to generate Jv for the current time step. The governing sub-module 73 operates on Jv, Vp, Cpi for the current time step to generate Ji for the current time step. The governing sub-module 74 operates on Jv for the current time step to generate the derivative of Vp for the current time step. The governing sub-module 75 operates on Jv, Ji, Cpi, Vp to generate the derivative of Cpi for the current time step. It is realized that by operating the FTM 52' from a start time (t=0) to an end time, a respective time series of values of Vp and Cpi are generated. Based on the time series of Cpi values, the FTM 52' extracts the Cpi values at the set of time points, resulting in [Cpi], which is output as dataset 57A for use by the conversion module 57 (cf. FIG. 5B).

When the operation of the PTM 52' is first started, the DES sub-module 71 obtains the intraperitoneal volume at the start time, Vp(0), and the concentrations of the solutes in the treatment fluid in the PC at the start time, Cpi(0), from the initial dataset 52A. In the example of FIG. 5C, the initial dataset 52A is provided by a start data module 76. The values of Vp(0), Cpi(0) are then supplied as dataset 71B at the start time (t=0). As understood from the governing functions ƒ1-ƒ4, sub-module 72 operates on LpS (and possibly fCpw), and sub-module 73 operates on LpS and $PS_{1 \ldots N}$ (and possibly fCpw). To extent that LpS, PSi and fCpw are included in the candidate property data 53B and thus are to be determined by the PT arrangement 50, the initial dataset 52A may comprise initial values for LpS, PSi and fCPw to be used by the sub-modules 72, 73, 75 when the operation of the PTM 52' is first started. In the example of FIG. 5C, the respective sub-module 72, 73 may retrieve the initial values $LpS_0$ and $PSi_0$ from the initial dataset 52A. The initial values $LpS_0$, $PSi_0$ may, for example, be obtained by the start data module 76 from the generic patient data 56B or the patient specific data 56C (FIG. 5A).

The initial values Vp(0), Cpi(0) may also be obtained by the start data module 76 from the generic patient data 56B or the patient specific data 56C (FIG. 5A). However, the use of generic patient data 56B may lower the accuracy of the resulting status parameter(s), if one or more of the initial values Cpi(0) differ significantly from the actual values of the patient. In some embodiments, to mitigate this potential problem, the start data module 76 is configured to run a simulation based upon the information about one or more recent regimens in the treatment history data 56A (FIG. 5A). The simulation may be performed by use of the governing functions ƒ1-ƒ4 to calculate Cpi(0) based on an assumed residual volume of the patient and considering the recent regimen(s). Initial values for the concentrations of the solutes in the residual volume for this simulation may be taken as plasma water concentrations, optionally slightly modified from plasma water by, for example, reducing the content of large solutes and/or by adjusting sodium and chloride according to Donnan equilibrium.

Alternatively, the start data module 76 may set the initial values Cpi(0) equal to the plasma water concentration, optionally while applying a reduction factor for large solutes such as albumin. In another alternative, the start data module 76 may set the initial values Cpi(0) equal to the concentration of the respective solute in the fresh treatment fluid.

When the PFA 53' has calculated candidate property data 53B based on the dataset 57A generated by the PTM 52' for the initial dataset 52A, the PTM 52' is again operated to generate a respective time series of values of Vp and Cpi. The PTM 52' may again use Vp(0) and Cpi(0) as initial values but will now use LpS and PSi in the candidate property data 53B from PFA 53' (FIG. 5B).

As shown in FIG. 4C, the residual volume may have a profound impact on the conductivity of the treatment fluid in the PC. This means that errors in the initial value Vp(0) may have a significant impact on the accuracy of the estimated concentration values [Cpi] and thereby on the estimated conductivity [Kp]. In some embodiments, to mitigate the impact of such errors, the PFA 53' is configured to include the intraperitoneal volume at one or more time points among the parameters that are fitted. In other words, Vp at one or more time points is included in the candidate property data 53B. In some embodiments, the intraperitoneal volume at the end of a drain cycle, i.e. the residual volume Vres, is included in the candidate property data 53B.

Figure 6A:
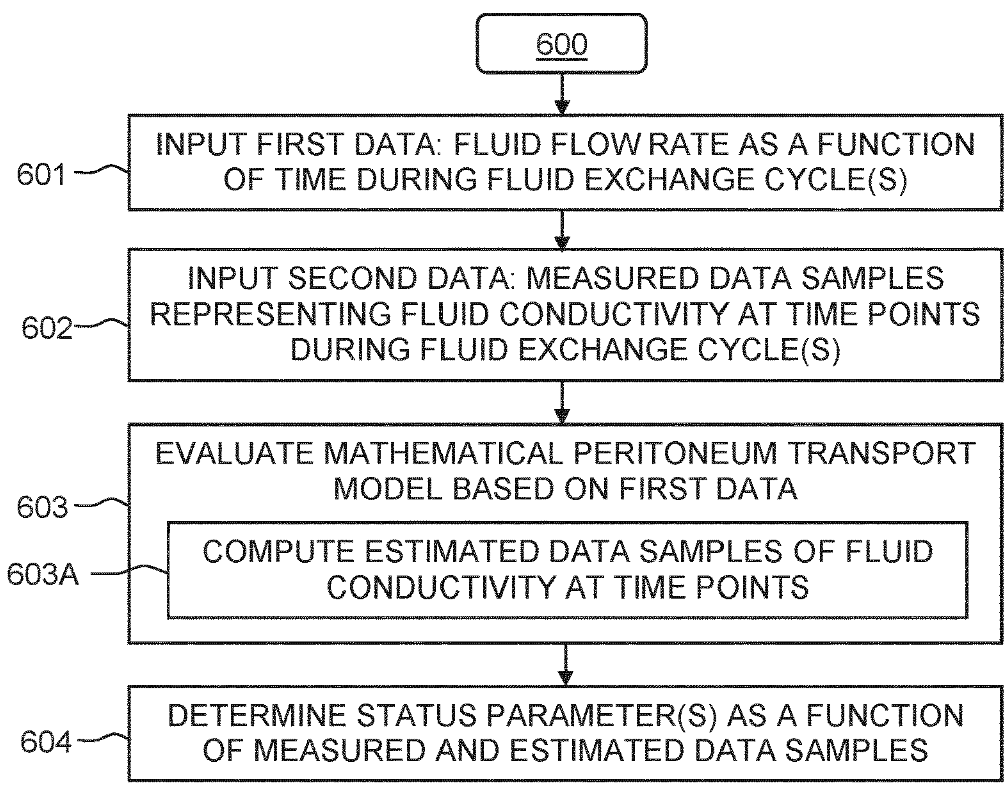
FIG. 6A is a flow chart of an example method for determining status parameter(s) of a PD patient.

FIG. 6A is a flow chart of an example method 600 for determining at least one status parameter of an individual undergoing PD dialysis. The example method 600 may be performed by the example PT arrangement 50 shown in FIGS. 5A-5C and described hereinabove. In step 601, first data is input. The first data is indicative of the flow rate as a function of time of treatment fluid into and out of the peritoneal cavity 31 (FIG. 3), via the peritoneal access 12' (FIG. 1) on the individual, during one or more fluid exchange cycles. The first data may correspond to or be included in the test regimen data 54A (FIG. 5A). In step 602, second data is input. The second data comprises measured data samples [Kp*] (FIG. 5B) representing conductivity of the treatment fluid in the peritoneal cavity 31 at two or more time points during the one or more fluid exchange cycles. The second data may correspond to or be included in the measurement data 54B (FIG. 5A). Step 603 evaluates a mathematical peritoneum transport model 52' (FIGS. 5A-5C) based on the first data and comprises a sub-step 603A of computing estimated data samples [Kp] (FIG. 5B) representing the conductivity of the treatment fluid in the peritoneal cavity 31 at the two or more time points. Step 604 determines the at least one status parameter as a function of the measured data samples [Kp*], given by the second data, and the estimated data samples [Kp], given by step 603.

It is realized that the example method 600 may be performed by a PT arrangement that is considerably different from the example PT arrangement 50 in FIGS. 5A-5C. Thus, the present disclosure is not limited to the specific combinations of features presented with reference to FIGS. 1-5. For example, it is conceivable to reduce the complexity of the governing functions ƒ1-ƒ4 so as to simplify the calculations to be performed by the PT arrangement 50, albeit possibly at the expense of accuracy. It may even be possible to define the governing functions so as to admit algebraic calculation of the status parameter(s) based on the measured and estimated data samples.

At the same time, it should be recognized that the foregoing examples comprise features that singly or in combination may provide distinct technical advantages, for example to increase accuracy, increase processing efficiency, etc.

In some embodiments, the at least one status parameter comprises one or more transport properties of the peritoneum. Knowledge of such a transport property enables detailed assessment of the status of the peritoneum.

In some embodiments, the at least one status parameter comprises a diffusion capacity of a solute through the peritoneum, and/or a filtration capacity of water through the peritoneum. Both of these transport properties are relevant indicators of the status of the peritoneum. As understood from the foregoing, the diffusion capacity may comprise a permeability surface area product, PSi, of an agent in the treatment fluid. The agent may be any solute present in the fresh or spent treatment fluid, for example an osmotic agent. As understood from the foregoing, the filtration capacity may comprise a hydraulic conductance, for example given by an ultrafiltration coefficient.

In some embodiments, the at least one status parameter comprises the volume of treatment fluid in the peritoneal cavity at a selected time point. For example, the selected time point may be at completion of the drain phase of at least one of the one or more fluid exchange cycles, resulting in residual volume. As described above with reference to FIG. 5C, the intraperitoneal volume at one or more time points may be included as a parameter that is determined based on the measured and estimated data samples. By proper selection of time point, it is thus possible to obtain an improved estimate of the residual volume. The residual volume is a relevant characteristic for assessing the status of the peritoneum and may also be used for optimizing the PD treatment.

In some embodiments, the at least one status parameter comprises a tonicity parameter of the individual, for example the above-mentioned scaling factor fCpw. Such a tonicity parameter may be used for assessing the status of the patient.

In some embodiments, as exemplified in FIGS. 5A-5C, the PT arrangement 50 comprises a parameter fitting algorithm 53', which is operable to determine a respective candidate value of a set of parameters included in the mathematical peritoneum transport model 52' to minimize a difference between the measured and estimated data samples. The set of parameters comprises the at least one status parameter. Thus, the respective status parameter may be given by the corresponding candidate value that minimizes the difference, at least to the extent that the difference is below a threshold. The use of a parameter fitting algorithm 53' enables the use of a more complex, and possibly more accurate, peritoneum transport model 52'.

In some embodiments, as exemplified in FIG. 5B, the set of parameters represents a diffusion capacity of one or more solutes through the peritoneum (e.g., PSi or fPS) and a filtration capacity of water through the peritoneum (e.g., LpS).

In some embodiments, as described with reference to FIG. 5B, the set of parameters further represents a tonicity of the individual (e.g. fCpw).

In some embodiments, as exemplified in FIGS. 5A-5C, the first computation module 52 is configured to alternately compute the estimated data samples, [Kp], based on the respective candidate value (cf. candidate property data 53B) of the set of parameter values alternately determined by the second computation module 53. The second computation module 53 may thus be configured to alternately determine the respective candidate value of the set of parameters based on the estimated data samples, [Kp], from the first computation module 52. The second computation module 53 may be configured to output the at least one status parameter when a convergence criterion is fulfilled or a time limit is reached. Thereby, the first and second computation modules 52, 53 are arranged to define the above-mentioned feedback control system that operates to iteratively find the best values for the set of parameters, and thereby also the best value for the at least one status parameter.

In some embodiments, as exemplified in FIG. 5C, the first computation module 52 is configured to compute, based on the first data (cf. test regimen data 54A) and by use of the mathematical peritoneum transport model 52', a time sequence of estimated amounts of treatment fluid in the peritoneal cavity for a time period during the one or more fluid exchange cycles. As understood from the foregoing description, the calculation of the time series of Vp values enables the calculation of corresponding Cpi values at high accuracy.

In some embodiments, the mathematical peritoneum transport model 52' is a three-pore model, TPM, for transport through the peritoneum. The TPM is an established and reliable model.

In some embodiments, the mathematical peritoneum transport model 52' is configured to account for ion transport by electrostatic force across the peritoneum caused by differences in amounts of dissolved ions on opposite sides of the peritoneum and reflection of large charged solutes by the peritoneum. An example of such a mathematical peritoneum transport model 52' is given in Appendix A. A further example of incorporation of electrostatic force in a peritoneum transport model is found in Chapter 17 (pp 33-36) of the publication "Analysis of Transvascular Transport Phenomena in the glomerular and peritoneal microcirculation", by Oberg, Carl, (1 ed.), Lund: Lund University: Faculty of Medicine, ISBN 978-91-7619-372-3. It is currently believed that more accurate results are achieved by accounting for the electrostatic force. It may be noted that there are alternative and/or simpler techniques for accounting for the ion transport by electrostatic force, for example by use of the so-called Donnan factor.

In some embodiments, as exemplified in FIG. 5C, the first computation module 52 comprises a differential equation solver (DES) sub-module 71 configured to calculate, for a current time step, the amount of treatment fluid (cf. 71B) in the peritoneal cavity based on a preceding temporal change in the amount of the treatment fluid in the peritoneal cavity (cf. 74B). The DES sub-module 71 may be further configured to calculate, for the current time step, a concentration of one or more solutes in the treatment fluid in the peritoneal cavity (cf. 71B) based on a preceding temporal change in the concentration of the one or more solutes in the treatment fluid in the peritoneal cavity (cf. 75B). As understood from the foregoing description, this enables calculation of a time series of Cpi values with high accuracy.

In some embodiments, as exemplified in FIG. 5C, the first computation module 52 further comprises a first change computation system, which is configured to compute the current temporal change in the amount of the treatment fluid in the peritoneal cavity (cf. 74B) as a function of a current concentration of the one or more solutes in the treatment fluid in the peritoneal cavity (cf. 71B) calculated by the DES sub-module 71, and a current amount of treatment fluid in the peritoneal cavity (cf. 71B) calculated by the DES sub-module 71. As understood from the foregoing description, this enables calculation of a time series of Cpi values with high accuracy.

In some embodiments, as exemplified in FIG. 5C, the first change computation system comprises a first flow rate computation sub-module 72, which is configured to compute a current flow rate of water through the peritoneum (cf. 72B) as a function the current amount of treatment fluid in the peritoneal cavity (cf. 71B) calculated by the DES sub-module 71. The first change computation system may further comprise a first change computation sub-module 74, which is configured to compute the current temporal change in the amount of the treatment fluid in the peritoneal cavity (cf. 74B) as a function of the current flow rate of water through the peritoneum (cf. 72B). As understood from the foregoing description, this enables calculation of a time series of Cpi values with high accuracy.

In some embodiments, as exemplified in FIG. 5C, the first computation module 52 further comprises a second change computation system, which is configured to compute the current temporal change in the concentration of the one or more solutes in the treatment fluid in the peritoneal cavity (cf. 75B) as a function of the current concentration of the one or more solutes in the treatment fluid in the peritoneal cavity (cf. 71B) calculated by the DES sub-module 71, and the current amount of treatment fluid in the peritoneal cavity (cf.

71B) calculated by the DES sub-module 71. As understood from the foregoing description, this enables calculation of a time series of Cpi values with high accuracy.

In some embodiments, as exemplified in FIG. 5C, the second change computation system comprises a second flow rate computation sub-module 73, which is configured to compute a current flow rate of the one or more solutes through the peritoneum (cf. 73B) as a function of the current concentration of the one or more solutes in the treatment fluid in the peritoneal cavity (cf. 71B) calculated by the DES sub-module 71, and the current amount of treatment fluid in the peritoneal cavity (cf. 71B) calculated by the DES sub-module 71. The second change computation system may further comprise a second change computation sub-module 75, which may be configured to compute the current temporal change in the concentration of the one or more solutes in the treatment fluid in the peritoneal cavity (cf. 75B) as a function of the current flow rate of the one or more solutes through the peritoneum (cf. 73B), the current flow rate of water through the peritoneum (cf. 72B), the current concentration of the one or more solutes in the treatment fluid in the peritoneal cavity (cf. 71B) calculated by the DES sub-module 71, and the current amount of treatment fluid in the peritoneal cavity (cf. 71B) calculated by the DES sub-module 71. As understood from the foregoing description, this enables calculation of a time series of Cpi values with high accuracy.

In some embodiments, as exemplified in FIG. 5B, the first computation module 52 is configured to generate a time sequence, [Cpi], of estimated concentration values of at least one solute in the treatment fluid in the peritoneal cavity, convert the time sequence of estimated concentration values to a time sequence of conductivity values, and determine the estimated data samples, [Kp], from the time sequence of conductivity values. The conversion from concentration values to conductivity values enables the first computation module 52 to apply a kinetic model of the solute concentration in the peritoneal cavity which in turn enables a physically accurate modeling of the impact of the status parameter(s) on the conductivity of the treatment fluid in the peritoneal cavity. Ultimately, this safeguards the accuracy of the determined status parameter(s).

In some embodiments, exemplified in FIG. 5C, the PT arrangement 50 is further arranged to receive fluid exchange data for the individual in a preceding time period before the one or more fluid exchange cycles (cf. 56A in FIG. 5A). The PT arrangement 50 may be further configured to estimate, based on the fluid exchange data, an initial concentration of one or more solutes, Cpi(0), in the treatment fluid in the peritoneal cavity at an evaluation starting point. The first computation module 52 may be configured to compute the estimated data samples, [Kp], based on the initial concentration. As understood from the foregoing, the estimation of the initial concentration values enables an improved accuracy of the estimated data samples, [Kp], since the initial concentration values, which are estimated from fluid exchange data for the individual in a preceding time period, are likely to be more representative of the patient at the evaluation starting point than generic concentration values.

The operation and use of the technique described in the foregoing will now be described with reference to simulation data shown in FIGS. 7-11.

Figures 7A, 7B:
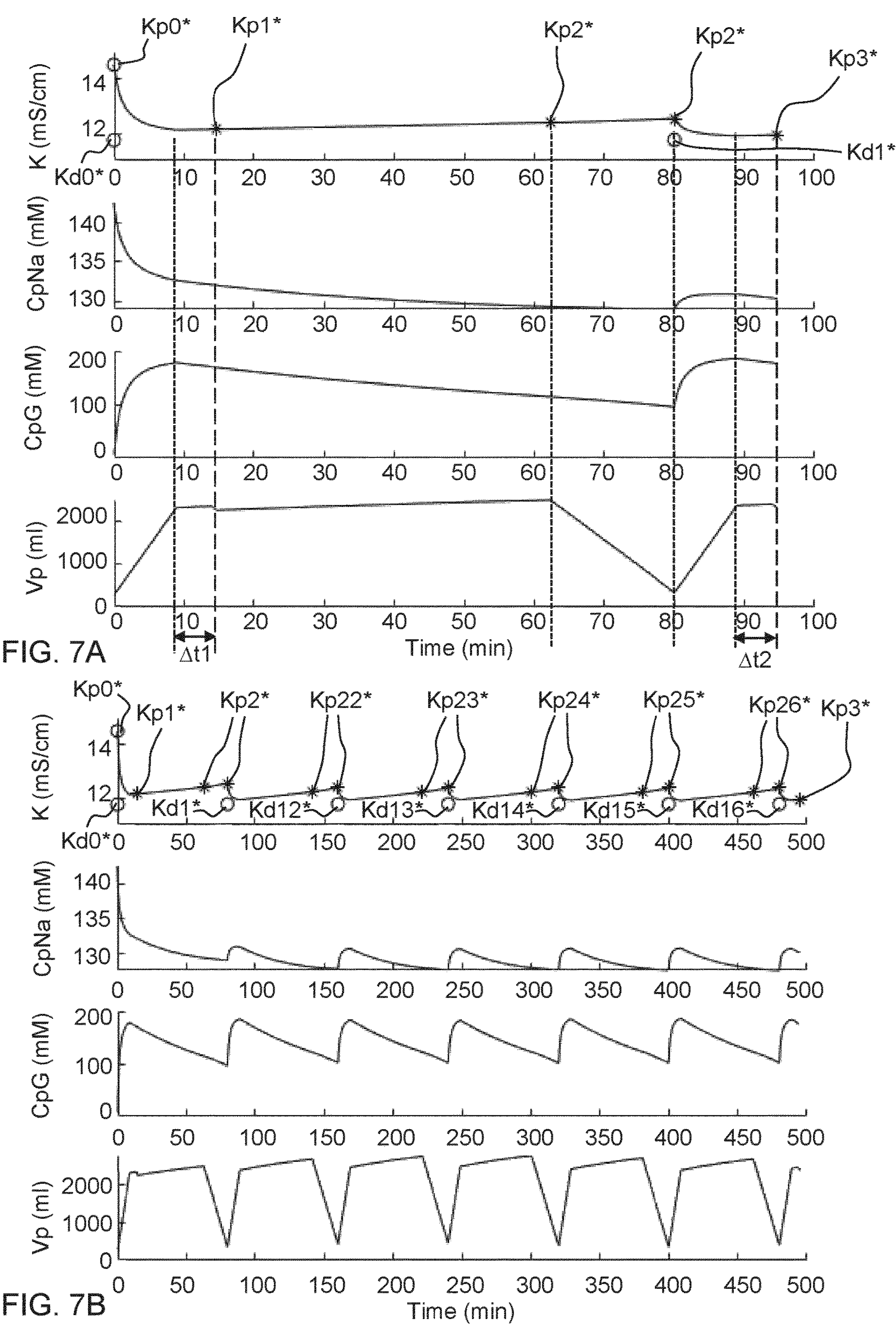
FIG. 7A is a combination of simulated plots of conductivity, sodium concentration, glucose concentration and intraperitoneal volume versus time, and indicates instances of conductivity measurement during a short test procedure.
FIG. 7B is a corresponding combination of simulated plots for a long test sequence.

FIGS. 7A-7B are graphs of example variables generated by the first computation module 52 for a simulated patient with known values of PSi, LpS, fCpw and Vres. FIG. 7A illustrates a short test procedure comprising, in sequence, a fill phase, a dwell phase, a drain phase, a fill phase, and part of a dwell phase. FIG. 7B illustrates a long test procedure comprising six complete fluid exchange cycles followed by a fill phase and part of a dwell phase. In each of FIG. 7A and FIG. 7B, the graphs illustrate, from top to bottom, the conductivity (K) of the treatment fluid in the peritoneal cavity, the concentration of sodium (CpNa) in the treatment fluid in the peritoneal cavity, the concentration of glucose (CpG) in the treatment fluid in the peritoneal cavity, and the intraperitoneal volume (Vp). The simulations have been made for test procedures that start at the end of an initial drain phase (not shown) and end a time period into a concluding dwell phase. The vertical dotted lines in FIG. 7A have been added to indicate the transition time points between the different phases. The variables Vp, CpNa and CpG are generated by the PTM 52' in the first computation module 52, with CpNa and CpG being examples of Cpi, and the variable K is generated by the conversion module 57 based on Cpi (including CpNa and CpG).

FIGS. 7A-7B also show examples of time points for measuring conductivity during the test procedure. In the short test procedure of FIG. 7A, data samples at five time points are illustrated. A data sample Kp0* is taken at the end of the initial drain phase, i.e. before the start of the first fill phase. A data sample Kp1* is taken in the following dwell phase, a predefined time period (Δt1) after completion of the first fill phase. A data sample Kp2* is taken during the following drain phase. This data sample may be taken at any well-defined time point during the drain phase, or at more than one time point. In FIG. 7A, data samples Kp2* are indicated at the start and the completion of the drain phase. A data sample Kp3* is taken a predefined time period (Δt2) after completion of the following fill phase, i.e. in the next dwell phase. In a non-limiting example, Δt1 and Δt2 may be in the range of 0-20 minutes or 0-10 minutes. FIG. 7A also indicates conductivity data samples Kd0* and Kd1*, which are measured on the fresh treatment fluid that is to be infused into the peritoneal cavity in the respective fill phase. As described above, the PTM 52' may operate on the nominal concentrations of solutes in the fresh treatment fluid (cf. of Eq. 3 in Appendix A). However, the accuracy of the status parameter(s) may be improved by operating on actual concentrations, if available, or an estimation of the actual concentrations in the fresh treatment fluid. For example, ready-made treatment fluid is produced with relatively large tolerance limits of the ingredients. For example, the concentration of sodium may have a tolerance limit of ±2.5%. This implies that the conductivity may vary from batch to batch of treatment fluid, introducing errors in the calculations of the status parameter(s). By measuring the conductivity (Kd0*) of the fresh treatment fluid, and knowing its nominal conductivity, the nominal concentrations may be adjusted to better represent the actual concentrations. This adjustment may be performed in different ways, as readily understood by the skilled person. In one example, the water fraction in the fresh treatment fluid may be calculated to minimize the difference between the nominal and measured conductivity while ensuring that the sum of charges in the treatment fluid is zero, whereupon the nominal concentrations are scaled by the water fraction.

Reverting to the PD arrangement 1 in FIG. 1, the data samples Kd0*, Kd1*, etc. may be measured by the sensor 14 or another conductivity sensor in the PD arrangement. If the same treatment fluid is used in all fluid exchange cycles, it may be sufficient to obtain only one measured data sample of the conductivity of the fresh treatment fluid.

In FIG. 7B, examples of data samples are illustrated for the long test procedure. Compared to FIG. 7A, Kp3* has been moved from the dwell phase after the first fluid exchange cycle to the dwell phase after the last completed fluid exchange cycle. The data samples Kd12*, Kd13*, Kd14*, Kd15*, Kd16* correspond to Kd1* and may be omitted if the treatment fluid is the same between fluid exchange cycles. The data samples Kp22*, Kp23*, Kp24*, Kp25*, Kp26* correspond to Kp2* and are measured in the respective fluid exchange cycle.

Reverting to the PD arrangement 1 in FIG. 1, the data samples may be measured by the sensor 14. It is realized that the data sample(s) Kp2* during the drain phase is readily obtained by the sensor 14 measuring the conductivity of the treatment fluid (effluent) while it is pumped from the peritoneal cavity through the drain line 13. The same applies to data sample Kp0*. The other data samples Kp1*, Kp3* may be obtained by the APD cycler 3 being operated to draw a small portion of treatment fluid out of the peritoneal cavity via the patient line 12 into the drain line 13 for measurement by the sensor 14. Alternatively, the data samples Kp0*, Kp1*, Kp3* may be measured by another conductivity sensor in the hydraulic circuit of the PD arrangement 1. The extraction of treatment fluid results in a small loss of treatment fluid in the peritoneal cavity, which is represented by Js(t) in FIG. 3 and shown as a slight decrease in Vp at the respective measurement time point in FIGS. 7A-7B.

The number of data samples that are obtained during the test procedure and used for calculation of the status parameters(s) depends on the required accuracy (confidence) of the status parameter(s), the number of status parameters and possibly the type of status parameter to be calculated. When a single status parameter is to be calculated, two data samples may be sufficient. The timing of the data samples may depend on the status parameter(s) to be calculated. It is currently believed that the use of data samples Kp2* and Kp3*, for example as represented in FIG. 7A, enables calculation of any one of the status parameters PSi, LpS, fCpw or Vres. By including one or both of Kp0* and Kp1*, for example as represented in FIG. 7A, accuracy may be significantly improved and/or a further status parameter may be calculated. It is also realized that the accuracy may be increased by performing the calculations for a test procedure that includes more than one complete exchange phase and by taking further data samples, for example as represented by one or more of data samples Kd12*, Kd13*, Kd14*, Kd15*, Kd16*, Kp22*, Kp23*, Kp24*, Kp25*, Kp26* in FIG. 7B.

Since the data samples are simplest to obtain during the drain phase, it may be desirable to make as much use of Kp2* as possible. As noted above, two or more time separated Kp2* samples may be used in the calculations. It has surprisingly been found that the accuracy of the status parameter(s) may be increased by generating the residual data 53A (FIG. 5B) to include not only a difference between one Kp2* sample and a corresponding simulated Kp2 sample, but also a difference between a measured temporal change in conductivity during the drain phase and a corresponding simulated temporal change. In one example, the measured temporal change is given by the conductivity difference between two Kp2* samples divided by the time between the Kp2* samples.

It may be noted that Kp1* need not be taken in the first exchange cycle, as shown in FIG. 7B, but may be taken in any subsequent exchange cycle. However, the change in measured conductivity between a drain phase and a subsequent dwell phase is expected to decrease during the test procedure, for example as seen in the top graph of FIG. 7B. It is currently believed that the calculations are improved by obtaining Kp1* in the first exchange cycle to thereby maximize the change in measured conductivity.

FIGS. 8A-8D present simulation results that have been generated for the implementation shown in FIGS. 5A-5C, with the candidate property data comprising PSi, LpS, fCpw and Vres, and with PSi being represented by the above-mentioned scaling factor fPS. The simulations have been performed for three different glucose compositions of the fresh treatment fluid, containing 1.36% w/v, 2.27% w/v and 3.86% w/v glucose, respectively. The simulations added a random error of 0.01 mS/cm (standard deviation) for the simulations of measured conductivity, and by adding a random error of 0.45% (standard deviation) to nominal flow rates. The simulations were made for patients belonging to the four different transporter types H, HA, LA, L, and for the short test procedure of FIG. 7A and the long test procedure of FIG. 7B.

Figure 8A:
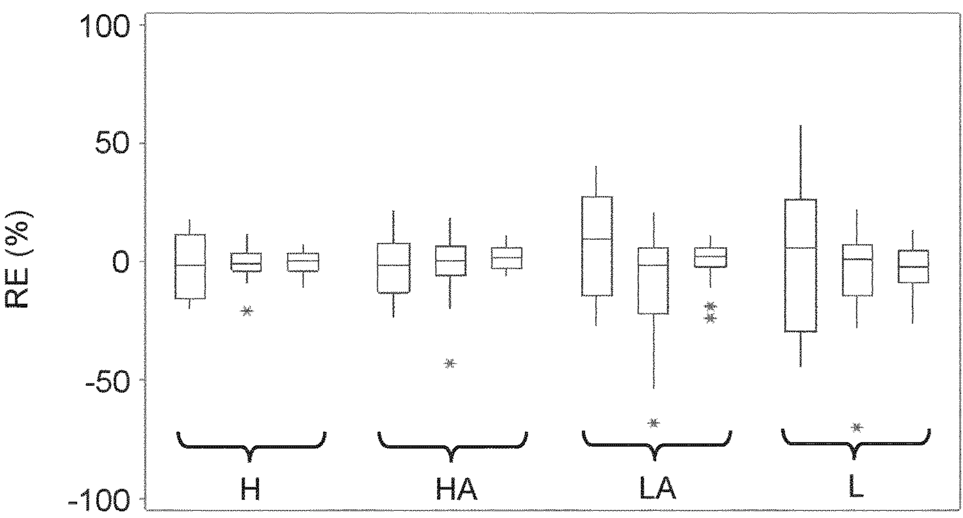
FIG. 8A is a box plot of relative error in PSG as determined based on the short test procedure of the type shown in FIG. 7A for different transporter types and different glucose concentrations.
Figure 8B:
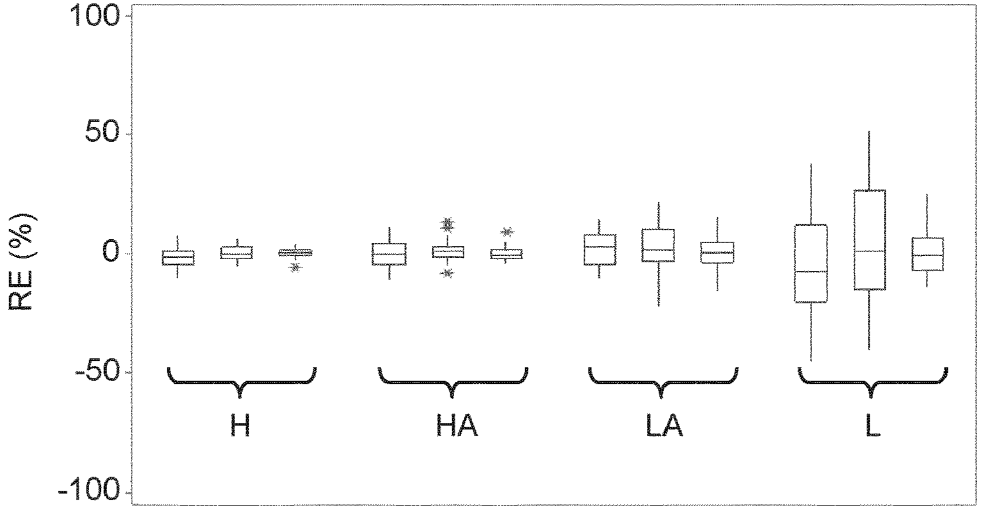
FIGS. 8B-8D are box plots of relative error in PSG, LpS and fCpw, respectively, as determined based on the long test procedure of the type shown in FIG. 7B for different transport types and different glucose concentrations.

The box plot in FIG. 8A illustrates the relative error (RE) in PSi for glucose for the respective transporter type, when calculated for the short test procedure. For the respective transporter type, the boxes represent, from left to right, fresh treatment fluid with glucose content of 1.36%, 2.27% and 3.86%. Reasonable accuracy is achieved for all transporter types and all glucose contents, with the accuracy being better for H and HA transporters. The box plot in FIG. 8B corresponds to FIG. 8A but is calculated for the long test procedure. As seen, the accuracy in PSi is significantly improved in the long test procedure.

Figure 8C:
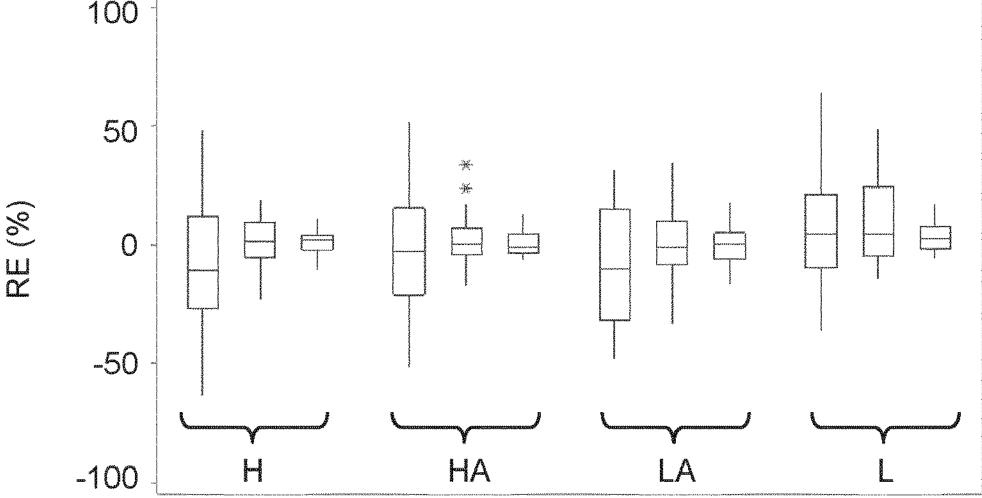

The box plot in FIG. 8C illustrates the relative error (RE) in LpS for the respective transporter type, when calculated for the long test procedure. As seen, good accuracy may be achieved for all transporter types and glucose contents.

Figure 8D:
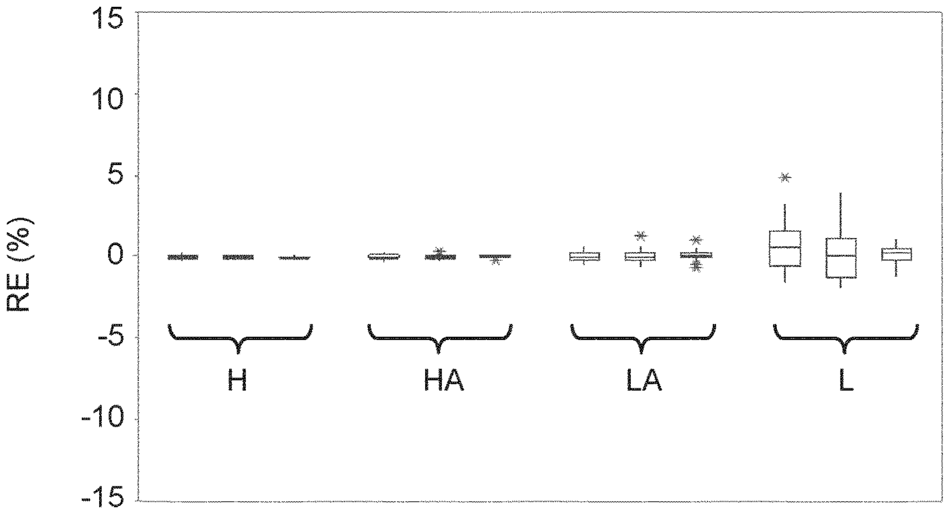

The box plot in FIG. 8D illustrates the relative error (RE) in fCpw for the respective transporter type, when calculated for the long test procedure. As seen, good accuracy may be achieved for all transporter types and glucose contents.

Figure 8E:
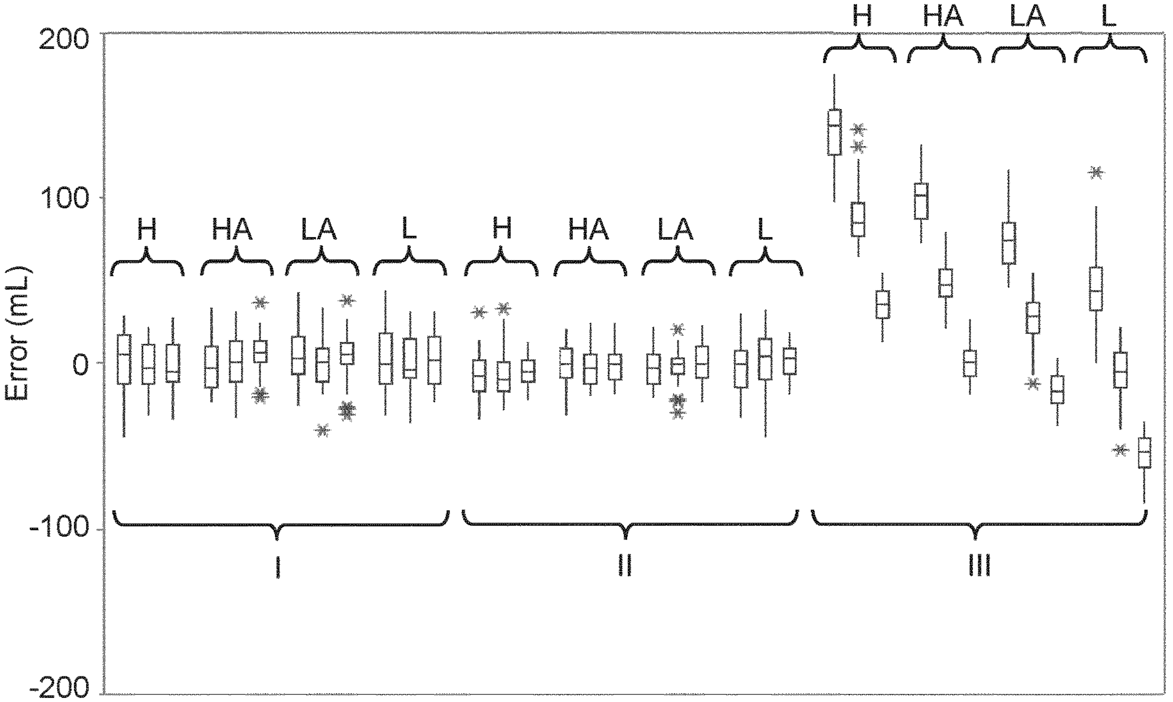
FIG. 8E is a box plot of absolute error in residual volume for different transporter types as calculated by different estimation techniques.

The box plot in FIG. 8E illustrates the absolute error (mL) in Vres for the respective transporter type, when calculated for the short test procedure (indicated by I) and the long test procedure (indicated by II). As seen, good accuracy may be achieved for all transporter types and glucose contents in both scenarios. The box plot also illustrates, by III, the absolute error (mL) in Vres when calculated according to a conventional dilution formula for different transporter types and glucose content. The dilution formula computes Vres as a function of the measured conductivity of the treatment fluid in the drain phase, the measured conductivity of the treatment fluid at the completion of the subsequent fill phase, the conductivity of the fresh treatment fluid and the amount of treatment fluid infused during the fill phase. Examples of such calculations are, for example, found in aforesaid EP2623139. The dilution formula does not account for the fact that the transfer through the peritoneum is ongoing at all times, i.e. also during the fill phase, and is therefore highly sensitive to transporter type and glucose content. This dependence is clearly seen in FIG. 8E, making the dilution formula largely unreliable for determining Vres.

The test procedure and the calculation technique described herein have many benefits. The test procedure and the calculation technique may be automated and may be performed at the point of care. Further, the test procedure may be performed as part of regular and prescribed therapy. This is stark contrast to Standard PET, which is a 4 h procedure requiring a specific composition of the fresh treatment fluid regardless of patient prescription.

The calculation technique is capable of determining small solute transport properties of the peritoneum, such as permeability surface area, PSi. Standard PET generates small solute transport properties as D/DO glucose and D/P creatinine for categorization into H/HA/LA/L, which is significantly less informative about the status of the peritoneum. Furthermore, the calculation technique may be configured to account for both charged and uncharged solutes, whereas Standard PET only measures glucose and creatinine, which are both uncharged.

The calculation technique is capable of determining the filtration capacity of water through the peritoneum, such as the ultrafiltration coefficient, LpS. The ability of Standard PET to take ultrafiltration properties into account when making the patient transport categorization H/HA/LA/L is limited. Standard PET involves measuring the total drained volume which may be used to determine fluid transport rates for the patient, after subtracting the infused volume. However, the error margin will be large due to lack of accurate information about the residual volume, as well as measurement errors in determining infused and withdrawn amounts of fluid. By the same token, Standard PET does not give information about the residual volume unless additional and unconventional procedures are added to the Standard PET test such as measuring the concentration of a component before and after the infusion, whereas the calculation technique presented herein is capable of determining the amount of treatment fluid in the peritoneal cavity at any time, for example at the completion of any drain cycle.

The test procedure and calculation technique may be run frequently, for example daily. Daily tests enable evaluation of the progression the status of the peritoneum both on long and short time scales, for example to detect possible membrane failure. Standard PET is at most done twice a year.

The calculation technique is capable of determining the tonicity of the patient, which is a measure of the overall plasma electrolyte concentration. The tonicity may be a useful property for patient diagnosis and/or categorization as well as to optimize prescription or detect shifts. Standard PET provides no such information.

Figures 9, 10A, 10B, 11A, 11B:
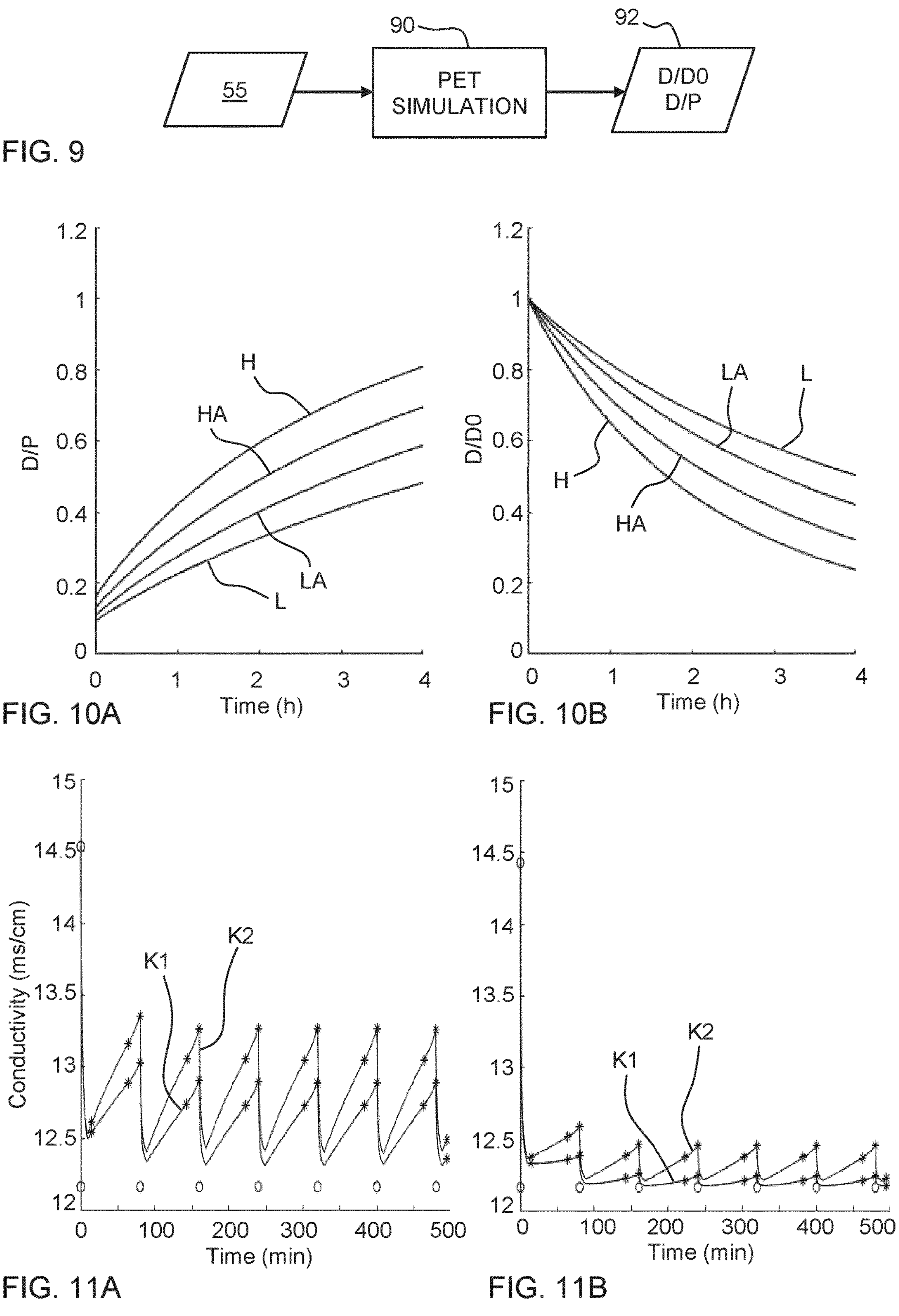
FIG. 9 is a block diagram of a simulation module for calculating simulated output parameters of a standardized PET procedure based on status parameter(s) as determined by a computation arrangement.
FIGS. 10A-10B are simulated plots of Standard PET parameters versus time calculated by the simulation module in FIG. 9.
FIGS. 11A-11B are simulated plots of treatment fluid conductivity versus time during PD treatment of a patient with normal and elevated PS values, for a low transporter type and a high transporter type, respectively.

FIG. 9 is a block diagram of an additional module 90 that may be included in the PT arrangement 50 to simulate a standardized PET procedure based on the status parameter(s) 55 calculated by the PT arrangement 50. The standardized PET procedure may be any PET procedure given by a standardized protocol (regimen, sampling, etc.), including but not limited to Standard PET. The simulation module 90 may comprise the PTM 52' and may be configured to operate the PTM 52' on test regimen data that is specific to the standardized PET procedure, including the timing and number of exchange cycles, the flow rates through the access 12' as a function of time, and composition of the fresh treatment fluid, for a patient having the characteristics according to the status parameter(s) calculated by the PT arrangement 50. The PTM 52' in module 90 is thereby operated to simulate the concentration of solutes in the treatment fluid in the peritoneal cavity, extract concentration values of specific solutes at specific time points, and calculate output parameters of the standardized PET procedure, for example D/DO and D/P for Standard PET. The parameter D/DO designates the relative change in glucose concentration in the treatment fluid in the peritoneal cavity between a starting time point and a specific time point. The parameter D/P may designate a concentration ratio for creatinine, at a specific time point, between the treatment fluid in the peritoneal cavity and the patient's plasma. Alternatively or additionally, the parameter D/P may be calculated for urea. The calculated parameter values of D/DO and/or D/P at one or more specific time points may be presented instead of or in addition to the status parameter(s), for example to a physician that wants to evaluate the status of the patient and its peritoneum based on the test procedure. FIG. 10A-10B are plots of D/DO and D/P for creatinine generated by a simulation module 90 comprising the PTM 52' as described herein, for a test regimen according to Standard PET in respect of H, HA, LA and L transporter types.

In some embodiments, the PT arrangement 50 is further configured to process one or more status parameters, as calculated for the test procedure, for detection of a potential failure of the peritoneum, for example caused by inflammation and/or infection, also known as peritonitis. Early detection of membrane failure enables medical personnel to take early measures to counteract peritonitis, which is beneficial for patient health and to avoid dropout of PD therapy. Upon detection of a potential failure, the PT arrangement 50 may be configured to generate a dedicated alarm, for example by activating a visual, audible or tactile feedback device, and/or generate an alert, for example an electronic message to a physician via any suitable communication channel. Any one of PSi, LpS, Vres and fCpw, or any combination thereof, may be monitored for detection of membrane failure.

In some embodiments, the PT arrangement 50 is configured to analyze a trend in the one or more status parameters for detection of a change, and to evaluate the change for detection of the potential failure. The trend may extend over several test procedures, and the change may be sudden, for example step-wise, or emerge over a longer time period, for example one or more weeks.

In some embodiments, the potential failure may be detected whenever the value of a status parameter exceeds a threshold value, which may be set in relation to one or more previously calculated values of the status parameter, for example in relation to a moving average. In one example, a potential failure may be detected when the value of the status parameter exceeds the moving average by at least 20%, 30%, 40% or 50%. To illustrate the effect of a 50% increase in PSi, FIGS. 11A-11B show simulation results of the conductivity of the treatment fluid in the peritoneal cavity with normal PSi values, represented as K1, and with the normal PSi values increased by 50%, represented as K2, where FIG. 11A is given for an H transporter, and FIG. 11B is given for an L transporter. It is realized that a membrane failure is likely to result in significant changes in the measured conductivity of the treatment fluid and is thereby also likely to be detectable from the status parameter(s) calculated by the PT arrangement 50.

Figure 6B:
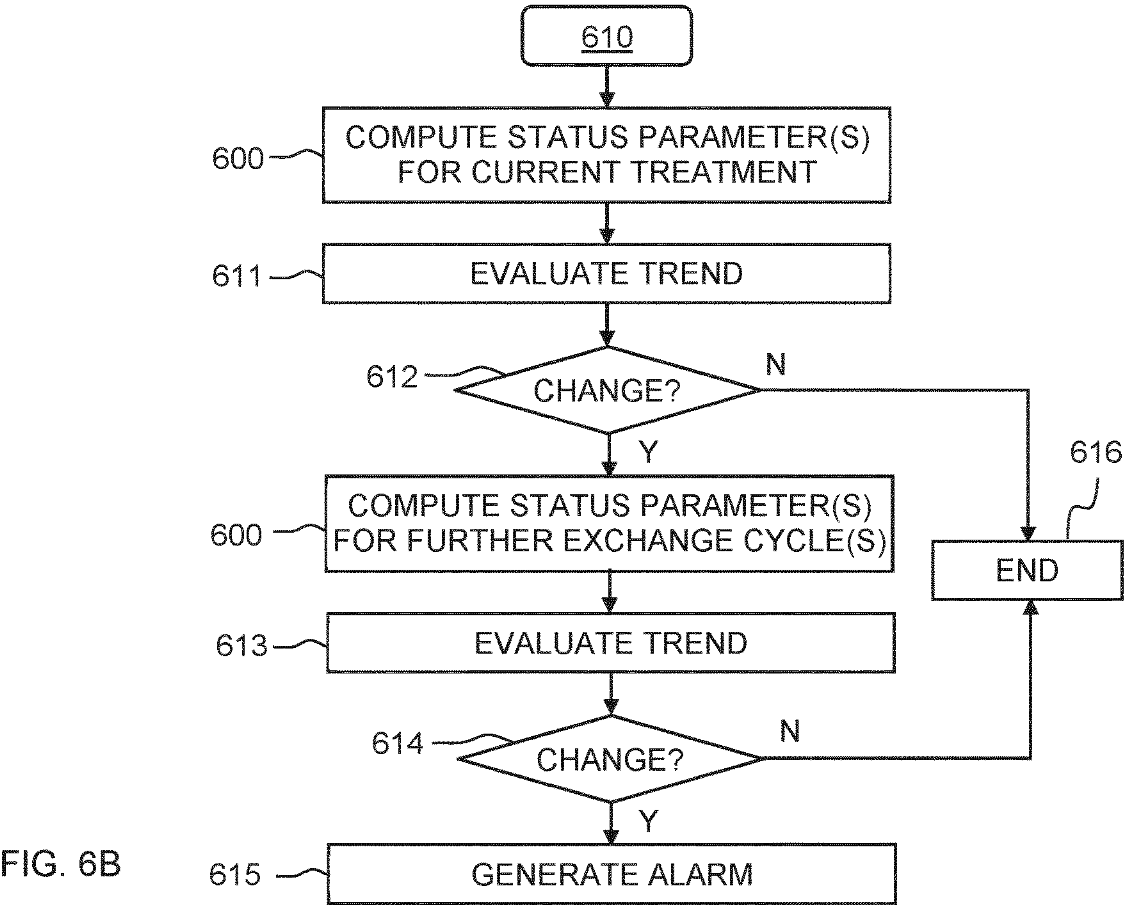
FIG. 6B is an example monitoring method for detecting peritoneal membrane failure.

FIG. 6B is a flow chart of an example monitoring method 610 for membrane failure. The example method 610 may be performed by the PT arrangement 50 and comprises a two-stage evaluation. In the first stage, one or more status parameters for a current test procedure are determined in accordance with the example method 600 in FIG. 6A, but only for a subset of the fluid exchange cycles of the current test procedure. Step 611 evaluates the trend of the status parameter(s) for detection of a first temporal change. If the first temporal change is not detected, step 612 proceeds to terminate the method 610. If the first temporal change is detected, step 612 proceeds to a second-stage evaluation, in which the same or any other status parameter(s) is(are) determined in accordance with the example method 600 in FIG. 6A while including conductivity measurements in further exchange cycles of the current test procedure. As understood from the foregoing, by increasing the number of fluid exchange cycles, the accuracy of the calculated status parameter(s) is increased. Step 613 evaluates the trend of the status parameter(s) for detection of a second temporal change, by a criterion that may be the same or different from the criterion used for detecting the first temporal change in step 611. If the second temporal change is not detected, step 614 proceeds to terminate the method 610. Otherwise, step 614 proceeds to generate an alarm. In some embodiments, step 611 is arranged to detect the first temporal change as a step-wise change in the status parameter(s) that occurs in the current test procedure. Since it is possible that such a step-wise change may be caused by measurement errors, the second-stage evaluation will reduce the risk of generating a false alarm.

As understood from the discussions above, the calculation technique described herein, using a mathematical peritoneum transport model, may be applied to estimate the IPV during PD treatment. This information may be monitored to ensure that the IPV is maintained within limits during a PD treatment. The IPV is largely unknown in contemporary APD, given that the residual volume in the PC may vary after a full drain or if a full drain is not performed, such as for instance during a tidal treatment. Therefore, there is a risk of overfilling the patient. To mitigate this risk, full drains are performed frequently during PD treatment. This, however, may increase the occurrence of so-called “drain pain”, which is a common complication in APD. The origin of drain pain is not completely understood by the scientific community. Drain pain is thought by some to be caused by application of negative pressure to the very sensitive parietal peritoneum towards the end of each drain cycle. This leads to referred pain, often quite unpleasant and felt in the rectal or genital areas. Others speculate that drain pain is related to negative suction on the external bowel wall. Regardless of origin, management of drain pain is a challenge.

With reference to FIG. 7A, the Applicant has found that it is possible to determine the IPV after a fill phase, based at least on a data sample taken during a drain phase (cf. Kp0* or Kp2*) and a data sample taken after the following fill phase, for example in the subsequent dwell phase (cf. Kp1* or Kp3*). Based on the IPV, the residual volume after the preceding drain phase may be determined. By this type of calculation, for example in the test procedure of FIG. 7B, the residual volume after one drain phase may be estimated and taken into account in the subsequent fill phase, by the APD cycler adjusting the infused volume to avoid overfilling, and in the subsequent drain phase, by the APD cycler adjusting the drained volume to mitigate the risk of drain pain. The calculation may be repeated for each sequence of a drain phase and a fill phase in a sequence of exchange cycles. It is thereby possible to estimate the residual volume intermittently during a test procedure that comprises a sequence of exchange cycles, for example for a respective exchange cycle. The Applicant has also found that it is possible to dispense with all but one of the data samples taken in the dwell phases. Thus, the residual volume after each drain phase in a sequence of exchange cycles may be estimated intermittently during the test procedure by use of a data sample taken during a drain phase (e.g., Kp0*), a data sample taken in the dwell phase after the subsequent fill phase (e.g., Kp1*), and data sample taken during at least one subsequent drain phase in the sequence of exchange cycles (e.g., Kp2*, Kp22*, Kp23*, etc.). Thus, in some embodiments, the PT arrangement (50 in FIG. 5A) may be configured to provide output data representing the estimated IPV, e.g. Vres, in an exchange cycle for receipt by the APD cycler (3 in FIG. 1), which is thereby caused to, based on the estimated IPV, perform an adjustment of at least one of a drain phase and a fill phase of a subsequent exchange cycle. The adjustment may involve decreasing or increasing the infused volume of treatment fluid.

As noted above, PD treatment may start with an initial drain if the patient is assumed to hold a large amount of treatment fluid in the PC when connected to the APD cycler. In some embodiments, the residual volume is estimated by the above-described calculations based at least on a data sample taken during the initial drain and a data sample taken after the subsequent fill phase. Thereby, the risk for overfilling and/or drain pain during PD treatment may be further mitigated.

The Applicant has further realized that it is possible to further mitigate the risk for overfilling and/or drain pain by providing an initial restricted probing cycle, abbreviated IRPC in the following. The IRPC comprises, in sequence, a drain phase and a fill phase. The IRPC may be performed by the APD cycler in advance of a PD treatment and is “restricted” in that only a fraction of the maximum fill volume is extracted from the peritoneal cavity. The maximum fill volume may be measured for the patient or a generic value. Based on two or more data samples of conductivity (or concentration) taken during the IRPC, the intraperitoneal volume (IPV) may be calculated by use of the mathematical peritoneum transport model, for example based on the equations in Appendix A and/or the governing functions as described above. An estimation of the IPV is thereby made available at the very beginning of the PD treatment. This allows the APD cycler to automatically adjust its operation based on the thus-estimated IPV, to mitigate the risk for drain pain and/or overfilling.

Figure 12A:
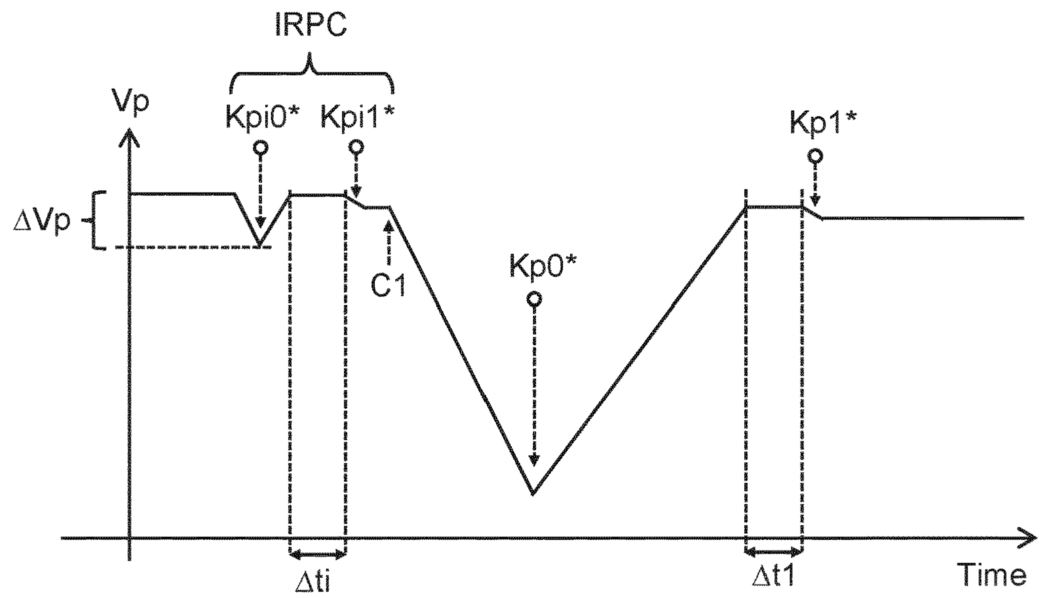
FIGS. 12A-12B are example plots of intraperitoneal volume and data samples taken over time according to a modified test procedure.

An example of an IRPC and its use will be described with reference to FIG. 12A, which shows the IPV (Vp) as a function of time. It is assumed that the residual volume is unknown when the patient is connected to the APD cycler. The IRPC starts by a drain phase, in which the APD cycler is operated to drain a restricted amount of treatment fluid from the PC, designated by ΔVp. In some embodiments, ΔVp is set to limit the risk of drain pain. For example, ΔVp may be set equal to or less than a nominal residual volume, which may be determined for the patient or for a group of patients, for example based on historic data. In some embodiments, ΔVp is set to be less than 10%-25% of the maximum fill volume. In some embodiments, ΔVp is in the range of 50-400 mL or 100-300 mL. The drain phase is followed by a fill phase, in which fresh treatment fluid in infused into the PC. To avoid the risk of overfilling, the amount of infused treatment fluid may be set equal to or less than ΔVp. During the IRPC, a first data sample Kpi0* is given by one or more measurements in the drain phase, by analogy with Kp0* and Kp2* above. A second data sample Kpi1* is taken a predefined time period (Δti) after completion of the fill phase. The time period Δti may be in the range of 0-20 minutes or 0-10 minutes. The second data sample Kpi1* may be obtained by operating the APD cycler to draw a small portion of treatment fluid out of the PC, by analogy with Kp1* and Kp3* above. Thus, Kpi1* results in a small loss of treatment fluid in the PC, as indicated in FIG. 12A. After a short calculation time, at time point Cl, the IPV (Vp) has been calculated, based on the extracted volume (ΔVp), the infused volume, Kpi0* and Kpi1*. In the illustrated example, the IPV is found to be large and the APD cycler operates to perform an initial drain in accordance with conventional practice. However, the initial drain will be controlled so as to mitigate drain pain, for example by setting the drained volume to ensure that the PC is not completely emptied by the initial drain. Likewise, the infused volume in the subsequent fill phase is set based on the estimated IPV and the drained volume to avoid overfilling. As indicated in FIG. 12A, the APD cycler may then proceed with a test procedure in accordance with the examples in FIGS. 7A-7B, by performing one or more exchange cycles while obtaining further data samples, for example Kp0*, Kp1*, etc. The calculations for the test procedure may produce one or more of the above-mentioned status parameters. As noted above, to determine the residual volume after the respective drain phase, it may be sufficient to obtain data samples during the drain phases, such as Kp0*, Kp2*, Kp22*, etc.

Figure 12B:
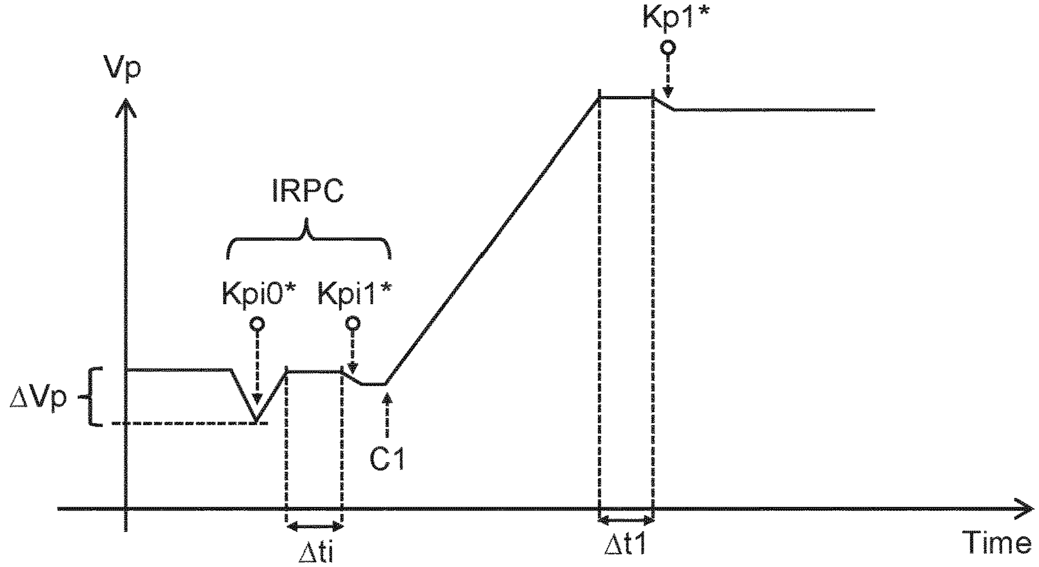

FIG. 12B shows another example of the use of the IRPC. FIG. 12B differs from FIG. 12A in that the patient starts with a small IPV. This is detected at time Cl, by the same calculations as in FIG. 12A. It is realized that the extraction of a restricted amount (ΔVp) reduces the risk for drain pain during the IRPC. In the illustrated example, since the IPV is found to be small, the APD cycler operates to perform a fill phase. Further, since the IPV at time point Cl is known, the fill phase may be controlled to prevent overfilling. The fill phase may be part of a test procedure as described hereinabove, and at least one of the above-mentioned status parameters may be produced based on a set of data samples taken during the test procedure. For example, Kp1* in FIG. 12B may (but need not) be included among the set of data samples.

As understood from FIGS. 12A-12B, the operation of the APD cycler may be controlled based on the IPV that is estimated for the IRPC. In some embodiments, the APD cycler is configured to perform a fill phase after the IRPC if the estimated IPV is less than a limit value (cf. FIG. 12B) and to perform a drain phase if the estimated IPV exceeds the limit value (cf. FIG. 12A). In one example, the limit value is in the range of 300-700 mL. The limit value may be patient-specific, for example set by the caretaker.

Thus, in some embodiments, the PT arrangement (50 in FIG. 5A) is configured to provide output data representing the estimated IPV, e.g. Vres, for receipt by the APD cycler (3 in FIG. 1), which is thereby caused to selectively initiate a drain phase or a fill phase after the IPRC depending on the estimated IPV.

As noted above, the calculation of the IPV may be repeated during the test procedure, resulting in calculated IPV values at discrete time points during the test procedure. Such embodiments enable the IPV to be tracked over time, for example to ensure that the IPV remains within limits. This may be important if the transport properties of the peritoneum are yet unknown, or if it is suspected that the transport properties have drifted, for example as a result of an infection.

It is to be understood that the calculation of the IPV may be additionally based on Kd0* (cf. FIGS. 7A-7B), i.e. measured conductivity/concentration of the fresh treatment fluid, instead of nominal conductivity/concentration.

In some embodiments, the calculation of IPV for the IRPC is performed as described hereinabove but with one or more of the transport properties of the peritoneum set to fixed values. Thus, in some embodiments, the PT arrangement is configured to set one or more transport properties of the peritoneum, as included in the mathematical peritoneum transport model (52' in FIG. 5A), to a fixed value when calculating the IPV. The skilled person realizes that the calculation will be simplified considerably by assuming fixed values of at least one of PSi, LpS and fCpw. For example, the complexity of the parameter fitting algorithm (53' in FIG. 5B) may be reduced. The fixed values may be given by historic values for the patient, for example produced by calculations for one or more preceding test procedures. Alternatively or additionally, the fixed values may be given by generic transport properties, for example average values for a group of patients. It is also conceivable that information from Standard PET performed on the patient may be used to adjust such generic transport properties to the patient.

Instead of using a mathematical peritoneum transport model to calculate the residual volume, as described in the foregoing, the residual volume may be estimated by use of a conventional dilution formula. Such an estimation may be performed for any sequence of a drain phase and a fill phase, for example during the IRPC or during a regular PD treatment. As described hereinabove, such a formula computes the residual volume as a function of three conductivity values: the conductivity of the treatment fluid in the drain phase, the conductivity of the treatment fluid at the completion of the subsequent fill phase (optionally after a delay period), and the conductivity of the fresh treatment fluid.

The Applicant also envisions further uses of an IPV that is estimated by use of a mathematical peritoneum transport model or a dilution formula, either for an IRPC in advance of a PD treatment, or for an initial exchange cycle of the PD treatment.

One such further use is to modify the composition of the fresh treatment fluid based on the residual volume, Vres, given by the estimated IPV. The fresh treatment fluid will mix with the residual volume in the PC, causing the treatment fluid to be diluted and potentially reducing the efficacy of the treatment. In some embodiments, the APD cycler comprises an algorithm that computes, based on the estimated Vres, an adjusted composition of the treatment fluid that approximately results in the prescribed composition when mixed with the residual volume inside the PC. The APD cycler may be further configured to obtain and infuse a treatment fluid with the adjusted composition during one or more fill phases subsequent to the IRPC. Thus, in some embodiments, the PT arrangement (50 in FIG. 5A) may be configured to provide output data representing Vres, for receipt by the APD cycler (3 in FIG. 1), which is thereby caused to adjust the composition of fresh treatment fluid produced by the APD cycler to account for the dilution of the fresh treatment fluid by the residual fluid in the PC, given by Vres. The composition may be adjusted to at least partly counteract the dilution.

Another use is to detect a problem with the peritoneal access based on the residual volume, Vres, given by the estimated IPV after a full drain. The access problem will result in an abnormal increase in Vres and may thus be detected and signaled by the APD cycler if Vres exceeds a patient safety limit, for example in the range of 600-900 mL. The access problem may be caused by a catheter obstruction or migration or by constipation. It may be noted that the detection of an access problem may but need not be based on an IPV determined for an IRPC. In a variant, the access problem is detected based on Vres that is determined for a test procedure, for example as described with reference to FIGS. 7A-7B. Thus, in some embodiments, the PT arrangement (50 in FIG. 5A) may be configured to evaluate the IPV for detection of a problem with the peritoneal access and to output an alert signal to alert a caretaker upon detection of an access problem.

Figure 13:
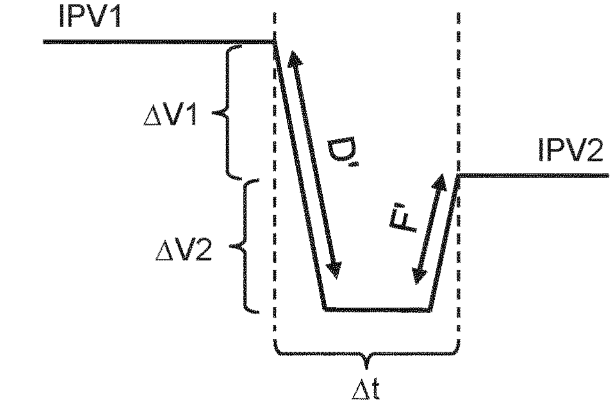
FIG. 13 is a plot of intraperitoneal volume versus time during an example sample pulling procedure.

FIG. 13 schematically illustrates a technique of sampling treatment fluid from the peritoneal cavity with minimum impact on the intraperitoneal volume. The sampling comprises an extraction phase D', a measurement phase, and a return phase F'. The duration of the sampling, At, may be about 1-5 minutes. In the extraction phase D', treatment fluid is drawn from the peritoneal cavity through lines of the PD arrangement to the conductivity sensor (cf. FIG. 1). The extracted amount of treatment fluid is ΔV1+ΔV2, for example 200 mL. In the return phase F', at least part of the extracted amount is pumped back into the peritoneal cavity, represented by ΔV2 in FIG. 13. By performing the return phase F', the impact of the sampling on the intraperitoneal volume is minimized since only ΔV1 is removed. Reverting to FIG. 3, it may be noted that Js(t) may reproduce the flow rate of treatment fluid as a function of time during the sample extraction when Js(t) is input to the PT arrangement 50 as part of the test regimen data (54A in FIG. 5A).

The PT arrangement 50 as described herein may be part of a PD arrangement, for example integrated into an APD cycler. Alternatively, the PT arrangement 50 may be implemented on a device that is separate from the PD arrangement 1. Such a device may be a local computer device or a remote computer device, which may or may not be located in the cloud. Further, the PT arrangement 50 may be configured to automatically obtain at least part of the input data shown in FIG. 5A. In some embodiments, the PT arrangement 50 may be configured and connected to obtain the measurement data (54B in FIG. 5A) from the conductivity sensor 14 or the APD cycler 3. In other embodiments, the measurement data 54B may be manually entered by an operator via an input unit connected to the PT arrangement 50.

The structures and methods disclosed herein are applicable to any modality of automated peritoneal dialysis (APD), including but not limited to Continuous Cyclic Peritoneal Dialysis (CCPD), Intermittent Peritoneal Dialysis (IPD), Tidal Peritoneal Dialysis (TPD), Continuous Flow Peritoneal Dialysis (CFPD). All of these modalities involve at least one fluid exchange cycle that comprises a fill phase, a dwell phase and a drain phase.

Figure 14:
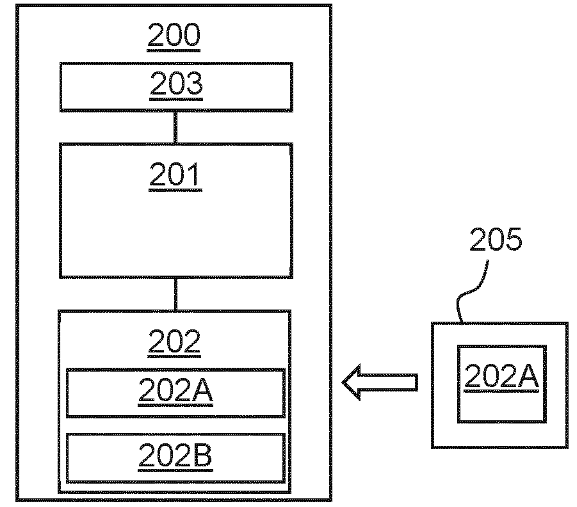
FIG. 14 is a block diagram of an example machine that may implement the methods, procedures and functions described herein.

The structures and methods disclosed herein may be implemented by hardware or a combination of software and hardware. In some embodiments, the hardware comprises one or more software-controlled computer resources. FIG. 14 schematically depicts such a computer resource 200, which comprises a processing system 201, computer memory 202, and a communication interface or circuit 203 for input and/or output of data. The communication interface 203 may be configured for wired and/or wireless communication. As understood from the forgoing, the computer resource 200 may or may not be part of an APD cycler. The processing system 201 may, for example, include one or more of a CPU ("Central Processing Unit"), a DSP ("Digital Signal Processor"), a GPU ("Graphics Processing Unit"), a microprocessor, a microcontroller, an ASIC ("Application-Specific Integrated Circuit"), a combination of discrete analog and/or digital components, or some other programmable logical device, such as an FPGA ("Field Programmable Gate Array"). A control program 202A comprising computer instructions is stored in the memory 202 and executed by the processing system 201 to implement logic that performs any of the methods, procedures, functions or steps described in the foregoing. The control program 202A may be supplied to the computer resource 200 on a computer-readable medium 205, which may be a tangible (non-transitory) product (e.g. magnetic medium, optical disk, read-only memory, flash memory, etc.) or a propagating signal. As indicated in FIG. 14, the memory 202 may also store control data 202B for use by the processing system 201, for example all or part of the test regimen data 54A, the treatment history data 56A, the generic patient data 56B, the patient specific data 56C or the solute property data 56D (FIG. 5A).

While the subject of the present disclosure has been described in connection with what is presently considered to be the most practical embodiments, it is to be understood that the subject of the present disclosure is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results.

In the following, items are recited to summarize some aspects and embodiments as disclosed in the foregoing.

Item 1. An arrangement for determining at least one status parameter of an individual (P) undergoing peritoneal dialysis, said arrangement comprising: an input (51) for receiving first data (54A) indicative of flow rate as a function of time of treatment fluid into and out of a peritoneal cavity (31), via a peritoneal access on the individual (P), during one or more fluid exchange cycles, wherein a respective fluid exchange cycle comprises a fill phase, a dwell phase and a drain phase, and second data (54B) comprising measured data samples ([Kp*]) representing concentration of one or more solutes in the treatment fluid in the peritoneal cavity (31) at two or more time points during the one or more fluid exchange cycles; a first computation module (52) configured to compute, based on the first data (54A) and by use of a mathematical model (52') of transport of water and solutes through a peritoneal membrane (30) in the peritoneal cavity (31), estimated data samples ([Kp]) representing the concentration of the one or more solutes in the treatment fluid in the peritoneal cavity (31) at said two or more time points; and a second computation module (53) configured to determine said at least one status parameter as a function of the measured data samples ([Kp*]) and the estimated data samples ([Kp]).

Item 2. The arrangement of item 1, wherein the at least one status parameter comprises a transport property of the peritoneal membrane (30).

Item 3. The arrangement of any preceding item, wherein the second computation module (53) comprises a parameter fitting algorithm (53') and is operable to determine, by use of the parameter fitting algorithm (53'), a respective candidate value (53B) of a set of parameters included in the mathematical model (52') to minimize one or more differences between the measured and estimated data samples ([Kp*], [Kp]), wherein the set of parameters comprises said at least one status parameter.

Item 4. The arrangement of item 3, wherein the second computation module (52) is further configured to compute, as a function of the measured and estimated data samples ([Kp*], [Kp]), a measured temporal change and an estimated temporal change in conductivity during the drain phase of the one or more fluid exchange cycles, and wherein the second computation module (52) is operable to determine, by use of the parameter fitting algorithm (53'), the respective candidate value (53B) to further minimize a difference between the measured temporal change and the estimated temporal change.

Item 5. The arrangement of item 3 or 4, wherein the set of parameters represents a diffusion capacity of one or more solutes through the peritoneal membrane (30) and a filtration capacity of water through the peritoneal membrane (30).

Item 6. The arrangement of item 4 or 5, wherein the set of parameters further represents a tonicity (fCpw) of the individual (P).

Item 7. The arrangement of any one of items 2-6, wherein the first computation module (52) is configured to repeatedly compute the estimated data samples ([Kp]) based on the respective candidate value (53B) of the set of parameter values determined by the second computation module (53), and the second computation module (53) is configured to repeatedly determine the respective candidate value (53B) of the set of parameters based on the estimated data samples ([Kp]) from the first computation module (52), wherein the second computation module (53) is configured to output the at least one status parameter when a convergence criterion is fulfilled or a time limit is reached.

Item 8. The arrangement of any preceding item, wherein the first computation module (52) is further configured to compute, based on the first data (54A) and by use of the mathematical model (52'), a time sequence of estimated amounts of treatment fluid in the peritoneal cavity (31) for a time period during the one or more fluid exchange cycles.

Item 9. The arrangement of any preceding item, wherein the mathematical model (52') is a three-pore model for transport through the peritoneal membrane (30).

Item 10. The arrangement of any preceding item, wherein the mathematical model (52') is configured to account for ion transport by electrostatic force across the peritoneal membrane (30) caused by differences in amounts of dissolved ions on opposite sides of the peritoneal membrane (30) and reflection of large charged solutes by the peritoneal membrane (30).

Item 11. The arrangement of any preceding item, which is further configured to evaluate the at least one status parameter for detection of a potential failure of the peritoneal membrane (30) and, upon detection of the potential failure, generate an alarm or an alert.

Item 12. The arrangement of item 11, which is configured to analyze a trend in the at least one status parameter for detection of a change, and evaluate the change for detection of the potential failure.

Item 13. The arrangement of item 11, which is configured to analyze a trend in the at least one status parameter for detection of a first temporal change; determine, upon detection of the first temporal change, the at least one status parameter at an increased accuracy; include the at least one status parameter at the increased accuracy in the trend; analyze the trend for detection of a second temporal change; and evaluate the second temporal change for detection of the potential failure.

Item 14. The arrangement of item 13, which is configured to determine the at least one status parameter at the increased accuracy by increasing the number of exchange cycles that are included in the first data (54A) and used by the first computation module (52) to compute the estimated data samples ([Kp]).

Item 15. The arrangement of any preceding item, which further comprises a simulation module (90), which is configured to compute, as a function of said at least one status parameter and at one or more time points given by a standardized PET procedure, at least one of: a concentration ratio (D/P) for at least one of urea or creatinine between the treatment fluid in the peritoneal cavity (30) and plasma in the individual, or a relative change (D/DO) in concentration of glucose in the treatment fluid in the peritoneal cavity (30) from a starting time point in the one or more fluid exchange cycles.

Item 16. The arrangement of any preceding item, wherein the second data (54B) further comprises one or more measured data samples (Kd0*, Kd1*, Kd12*, Kd13*, Kd14*, Kd15*, Kd16*) representing concentration of the one or more solutes in the treatment fluid that is infused into the peritoneal cavity (30) during the fill phase of the one or more fluid exchange cycles.

Item 17. The arrangement of any preceding item, wherein the first computation module (52) comprises a differential equation solver sub-module (71) configured to calculate, from an initial time point to an end time point, an amount (71B) of treatment fluid in the peritoneal cavity (31) from the initial time point to the end time point including intermediate time steps, and to calculate a concentration (71B) of one or more solutes in the treatment fluid in the peritoneal cavity (31) from the initial time point to the end time point including the intermediate time steps.

Item 18. The arrangement of item 17, wherein the differential equation solver sub-module (71) is configured to calculate, for a respective time step, the amount (71B) of treatment fluid in the peritoneal cavity (31) based on a preceding temporal change (74B) in the amount of the treatment fluid in the peritoneal cavity (31), and to calculate, for the respective time step, a concentration (71B) of one or more solutes in the treatment fluid in the peritoneal cavity (31) based on a preceding temporal change (75B) in the concentration of the one or more solutes in the treatment fluid in the peritoneal cavity (31).

Item 19. The arrangement of item 18, wherein the first computation module (52) further comprises a first change computation system (72, 74), which is configured to compute, for the respective time step, a temporal change (74B) in the amount of the treatment fluid in the peritoneal cavity (31) as a function of the concentration (71B) of the one or more solutes in the treatment fluid in the peritoneal cavity (31) calculated by the differential equation solver sub-module (71) for the respective time step, and the amount (71B) of treatment fluid in the peritoneal cavity (31) calculated by the differential equation solver sub-module (71) for the respective time step.

Item 20. The arrangement of item 19, wherein the first change computation system (72, 74) comprises a first flow rate computation sub-module (72), which is configured to compute, for the respective time step, a flow rate (72B) of water through the peritoneal membrane (30) as a function the amount (71B) of treatment fluid in the peritoneal cavity (31) calculated by the differential equation solver sub-module (71) for the respective time step, and wherein the first change computation system (72, 74) further comprises a first change computation sub-module (74), which is configured to compute the temporal change (74B) in the amount of the treatment fluid in the peritoneal cavity (31) as a function of the flow rate (72B) of water through the peritoneal membrane (30).

Item 21. The arrangement of item 19 or 20, wherein the first computation module (52) further comprises a second change computation system (73, 75), which is configured to compute, for the respective time step, a temporal change (75B) in the concentration of the one or more solutes in the treatment fluid in the peritoneal cavity (31) as a function of the concentration (71B) of the one or more solutes in the treatment fluid in the peritoneal cavity (31) calculated by the differential equation solver sub-module (71) for the respective time step, and the amount (71B) of treatment fluid in the peritoneal cavity (31) calculated by the differential equation solver sub-module (71) for the respective time step.

Item 22. The arrangement of item 21, wherein the second change computation system (73, 75) comprises a second flow rate computation sub-module (73), which is configured to compute, for the respective time step, a flow rate (73B) of the one or more solutes through the peritoneal membrane (30) as a function of the concentration (71B) of the one or more solutes in the treatment fluid in the peritoneal cavity (31) calculated by the differential equation solver sub-module (71) for the respective time step, and the amount (71B) of treatment fluid in the peritoneal cavity (31) calculated by the differential equation solver sub-module (71) for the respective time step, and wherein the second change computation system (73, 75) further comprises a second change computation sub-module (75), which is configured to compute the temporal change (75B) in the concentration of the one or more solutes in the treatment fluid in the peritoneal cavity (31) as a function of the flow rate (73B) of the one or more solutes through the peritoneal membrane (30), the flow rate (72B) of water through the peritoneal membrane (30), the concentration (71B) of the one or more solutes in the treatment fluid in the peritoneal cavity (31) calculated by the differential equation solver sub-module (71) for the respective time step, and the amount (71B) of treatment fluid in the peritoneal cavity (31) calculated by the differential equation solver sub-module (71) for the respective time step.

Item 23. The arrangement of any preceding item, wherein the measured data samples ([Kp*]) comprise measured conductivity values.

Item 24. The arrangement of any preceding item, wherein the first computation module (52) is configured to generate a time sequence ([Cpi]) of estimated concentration values of at least one solute in the treatment fluid in the peritoneal cavity (31), convert the time sequence ([Cpi]) of estimated concentration values to a time sequence of conductivity values, and determine the estimated data samples ([Kp]) from the time sequence of conductivity values.

Item 25. The arrangement of any preceding item, wherein the one or more fluid exchange cycles comprises two consecutive exchange cycles, wherein said two or more time points comprise a time point during the drain phase of a first fluid exchange cycle, and a time point during the dwell phase of a second fluid exchange cycle following upon the first exchange cycle.

Item 26. The arrangement of item 25, wherein said two or more time points further comprise at least one of: a time point during the dwell phase of the first fluid exchange cycle, or a time point during a drain phase preceding first fluid exchange cycle.

Item 27. The arrangement of any preceding item, wherein the input (51) is further arranged to receive fluid exchange data for the individual (P) in a preceding time period before the one or more fluid exchange cycles, and wherein the arrangement is further configured to estimate, based on the fluid exchange data, an initial concentration of one or more solutes in the treatment fluid in the peritoneal cavity (31) at an evaluation starting point, and wherein the first computation module (52) is configured to compute the estimated data samples ([Kp]) based on the initial concentration.

Item 28. The arrangement of any preceding item, wherein the at least one status parameter comprises at least one of: a diffusion capacity of a solute through the peritoneal membrane (30), or a filtration capacity of water through the peritoneal membrane (30).

Item 29. The arrangement of item 28, wherein the diffusion capacity of a solute comprises a permeability surface area product (PSi) of an agent in the treatment fluid, and the filtration capacity of water comprises a hydraulic conductance (LpS).

Item 30. The arrangement of any preceding item, wherein the at least one status parameter comprises a volume of treatment fluid in the peritoneal cavity (31) at a selected time point.

Item 31. The arrangement of item 30, wherein the selected time point corresponds to a completion of the drain phase of at least one of the one or more fluid exchange cycles.

Item 32. The arrangement of item 30 or 31, wherein the measured data samples in the second data (53B) comprise a first data sample taken during a drain phase and a second data sample taken after completion of a fill phase subsequent to the drain phase, and wherein the second computation module (53) is configured to determine the volume of treatment fluid in the peritoneal cavity (31) at the selected time point.

Item 33. The arrangement of item 32, wherein the first and second data samples are taken during an initial probing cycle (IRPC) which comprises the drain phase and the fill phase and in which a restricted amount ($\Delta$Vp) of treatment fluid in the peritoneal cavity (31) is extracted in the drain phase, the restricted amount ($\Delta$Vp) corresponding to a fraction of a maximum fill volume of the peritoneal cavity (31).

Item 34. The arrangement of item 33, wherein the restricted amount is less than 10%-25% of the maximum fill volume.

Item 35. The arrangement of item 33 or 34, wherein the restricted amount is in the range of 50-400 mL or 100-300 mL.

Item 36. The arrangement of any one of items 33-35, which is configured to provide output data representing the volume of treatment fluid in the peritoneal cavity (31), for receipt by a peritoneal dialysis arrangement (3) that is operated to perform the peritoneal dialysis, such that the peritoneal dialysis arrangement (3) is caused to initiate a drain phase after the initial probing cycle (IPRC) if the volume of treatment fluid is above a limit value, and to initiate a fill phase after the initial probing cycle (IPRC) if the volume of treatment fluid is below the limit value.

Item 37. The arrangement of any one of items 32-36, wherein the measured data samples in the second data (54B) further comprise a data sample taken during a subsequent drain phase, and wherein the second computation module (53) is further configured to determine the volume of treatment fluid in the peritoneal cavity (31) at the end of the subsequent drain phase.

Item 38. The arrangement of any one of items 30-37, which is configured to set one or more transport properties of the peritoneum (31), as included in the mathematical model (52'), to a fixed value when determining the volume of treatment fluid in the peritoneal cavity (31) at the selected time point.

Item 39. The arrangement of any one of items 30-38, which is configured to, intermittently during the peritoneal dialysis, determine and output the volume of treatment fluid for a respective fluid exchange cycle.

Item 40. The arrangement of item 39, which is configured to provide output data representing the volume of treatment fluid for the respective fluid exchange cycle, for receipt by a peritoneal dialysis arrangement (3) that is operated to perform the peritoneal dialysis, such that the peritoneal dialysis arrangement (3) is caused to, based on the volume of treatment fluid for the respective fluid exchange cycle, adjust at least one of a drain phase and a fill phase of a fluid exchange cycle subsequent to the respective fluid exchange cycle.

Item 41. The arrangement of any one of items 30-40, which is further configured to evaluate the volume of treatment fluid in the peritoneal cavity (31) at the selected time point for detection of a problem with the peritoneal access, and output an alert signal when the problem is detected.

Item 42. The arrangement of any one of Items 30-41, which is configured to provide output data representing the volume of treatment fluid in the peritoneal cavity (31) after completion of a drain phase, for receipt by a peritoneal dialysis arrangement (3) that is operated to perform the peritoneal dialysis, such that the peritoneal dialysis arrangement (3) is caused to adjust a composition of fresh treatment fluid produced by the peritoneal dialysis arrangement (3) to account for a dilution of the fresh treatment fluid by the volume of treatment fluid in the peritoneal cavity (31).

Item 43. The arrangement of any preceding item, wherein the at least one status parameter comprises a tonicity parameter (fCpw) of the individual (P).

Item 44. A peritoneal dialysis arrangement, comprising: an extracorporeal fluid circuit (3*b*) that is connectable to a peritoneal access of an individual (P) for conveying treatment fluid from/to a peritoneal cavity (31); at least one sensor device (14), which is arranged in the extracorporeal fluid circuit (3*b*) and configured to provide data samples representative of concentration of one or more solutes in the treatment fluid; a control apparatus (3*a*) configured to operate the extracorporeal fluid circuit (3*b*) and obtain the data samples from the sensor device (14); and an arrangement in accordance with any one of items 1-31, which is connected to receive the first and second data from the control apparatus (3*a*).

Item 45. A method of determining at least one status parameter of an individual undergoing peritoneal dialysis, said method comprising: obtaining (601) first data indicative of flow rate as a function of time of treatment fluid into and out of a peritoneal cavity, via a peritoneal access on the individual, during one or more fluid exchange cycles, wherein a respective fluid exchange cycle comprises a fill phase, a dwell phase and a drain phase; obtaining (602) second data comprising measured data samples representing concentration of one or more solutes in the treatment fluid in the peritoneal cavity at two or more time points during the one or more fluid exchange cycles; computing (603, 603A), based on the first data and by use of a mathematical model of transport of water and solutes through a peritoneal membrane in the peritoneal cavity, estimated data samples representing the concentration of the one or more solutes in the treatment fluid in the peritoneal cavity at said two or more time points; and determining (605) said at least one status parameter as a function of the measured data samples and the estimated data samples.

Item 46. A computer-readable medium comprising computer instructions (202A) which, when executed by one or more processors (201), cause the one or more processors (201) to perform the method of item 45.

Item 47. A monitoring method comprising: operating the arrangement of any one of items 1-43 to determine the at least one status parameter; and evaluating the at least one status parameter for detection of a potential failure of the peritoneal membrane.

APPENDIX A

The change in intraperitoneal volume is given by:

$$\frac{dV_p}{dt} = J_v(t) + J_f(t) - J_d(t) - J_s(t) - L \tag{1}$$

with $J_f(t)$ being the flow rate during the fill phase(s), $J_d(t)$ being the flow rate during the drain phase(s), $J_s(t)$ being the fluid loss during sample extraction, and L being the lymphatic absorption, which may be assumed to be constant, for example at 0.3 mL/min.

The total fluid flow over the peritoneal membrane is the sum of the flow through the aquaporins (m1), small pores (m2) and large pores (m3):

$$J_v(t) = J_{v,m1}(t) + J_{v,m2}(t) + J_{v,m3}(t) = \sum_{m=1}^{3}\left(A_f(t)\cdot\alpha_m\cdot L_pS\cdot\left(\Delta P(t) - RT\sum_{i=1}^{N}\varphi_i\cdot\sigma_{m,i}\cdot(C_{bi} - C_{pi}(t))\right)\right) \tag{2}$$

with $\alpha_m$ being the fraction of hydraulic conductance for the respective pore type, which may be assumed to be $\alpha_1=0.02$, $\alpha_2=0.90$, and $\alpha_3=0.08$, and with R being the ideal gas constant, T being the body temperature, and N being the number of different solutes.

The area factor, $A_f(t)$, may be introduced to account for the fact that the effective area for exchange will depend on the volume of fluid in the peritoneal cavity. The area factor may be given by:

$$A_f(t) = \frac{16.18\cdot\left(1 - e^{-0.00077\cdot V_p(t)}\right)}{13.3187}$$

The hydrostatic pressure difference between the peritoneal cavity and the capillaries, $\Delta P(t)$, may be calculated as $\Delta P(t)=P_{cap}(t)-IPP(t)$, where IPP(t) is the intraperitoneal pressure, which may be assumed to be a function of the intraperitoneal volume by:

$$IPP(T) = 4.7 + \frac{V_p(t)}{690}$$

The capillary pressure, $P_{cap}(t)$, may be set to be dependent on the mean arterial pressure, MAP, and the venous pressure, which may be assumed to be equal to IPP(t):

$$P_{cap}(t) = \frac{1}{9}\cdot MAP + \frac{8}{9}\cdot IPP(t)$$

The osmotic coefficient for the different solutes, $\varphi_i$, may be given by tabulated values, and the reflection coefficient for the different solutes, $\sigma_{m,i}$, may be given by:

$$\sigma_{m,i} = 1 - \frac{(1-\lambda_{m,i})^2\cdot\left(2-(1-\lambda_{m,i})^2\right)\cdot\left(1-\frac{\lambda_{m,i}}{3}\right)}{1 - \frac{\lambda_{m,i}}{3} + \frac{2}{3}\lambda_{m,i}^2}$$

where $\lambda_{m,i}$ is the quotient between the hydrodynamic radius of solute i, and the pore radius of the respective pore type (m=1, 2, 3). The hydrodynamic radius of the different solutes is an effective measure of the size, which is dependent on molecular mass/geometry as well as charge. It may also be noted that for aquaporins, $\sigma_{1,i}=1$.

The concentration differentials for each solute are dependent on the flow of solute and the dilution from fluid flow over the membrane as well as dilution during the fill phase(s):

$$\frac{dC_{pi}}{dt} = \frac{J_i(t)}{V_p(t)} - C_{pi}(t) \cdot \frac{J_v(t) + J_f(t)}{V_p(t)} + \frac{C_{Ii} \cdot J_f(t)}{V_p(t)} \tag{3}$$

with $C_{Ii}$ being the concentration of solute i in the fresh treatment fluid. The flow of solute i is given by:

$$J_i(t) = \sum_{m=2}^{3} A_f(t) \cdot PS_{i,m} \cdot Pe_{i,m}(t) \cdot \frac{C_{bi} - C_{pi}(t) \cdot e^{-Pe_{i,m}(t)}}{1 - e^{-Pe_{i,m}(t)}} \tag{4}$$

with $Pe_{i,m}(t)$ being the dimensionless Peclet number (convective through diffusive) for solute i through pore type m, calculated by:

$$Pe_{i,m}(t) = \frac{J_{v,m}(t) \cdot (1 - \sigma_{i,m})}{A_f(t) \cdot PS_{i,m}} - z_i \cdot \Delta E(t)$$

with $\sigma_{i,m}$ being the reflection coefficient of solute i at pore type m, which may be given by tabulated values. The last term is the electrostatic effect from the charge of the solute, $z_i$, and the potential, $\Delta E(t)$, across the membrane 30. However, as there will be no current between the peritoneal cavity 31 and the blood side 32:

$$\sum_i (J_{i,m2}(t) + J_{i,m3}(t)) \cdot z_i = 0$$

with $J_{i,m2}(t)$ and $J_{i,m3}(t)$ being the flow of solute i through small pores (m2) and large pores (m3), respectively. This means that at each time point there will be a potential $\Delta E(t)$ that satisfies zero current. The magnitude of the potential, and thus $Pe_{i,m}(t)$, may be determined by use of any suitable root-finding algorithm, for example a bracketing method such as a bisection method, or an iterative method such as by Newton's method or a Newton-like method.

The invention claimed is:

1. An arrangement for determining at least one status parameter of an individual undergoing peritoneal dialysis, the arrangement comprising:

at least one sensor arranged in a fluid circuit and configured to provide data samples representative of a concentration of one or more solutes in a treatment fluid flowing through the fluid circuit;

an input for receiving:

first data indicative of a flow rate as a function of time of the treatment fluid into and out of a peritoneal cavity, via a peritoneal cavity access of the individual, during one or more fluid exchange cycles, wherein each fluid exchange cycle comprises a fill phase, a dwell phase, and a drain phase, and second data from the at least one sensor comprising measured data samples representing the concentration of one or more solutes in the treatment fluid in the peritoneal cavity at two or more time points during the one or more fluid exchange cycles;

a first computation module configured to compute, based on the first data and by use of a mathematical model of a transport of water and solutes through a peritoneal membrane in the peritoneal cavity, estimated data samples representing the concentration of the one or more solutes in the treatment fluid in the peritoneal cavity at the two or more time points; and a second computation module configured to determine the at least one status parameter by comparing the measured data samples in the second data and the estimated data samples computed by the first computation module.

2. The arrangement of claim 1, wherein the at least one status parameter comprises a transport property of the peritoneal membrane.

3. The arrangement of claim 1, wherein the second computation module comprises a parameter fitting algorithm and is operable to determine, by use of the parameter fitting algorithm, a respective candidate value of a set of parameters included in the mathematical model to minimize one or more differences between the measured data samples and the estimated data samples, wherein the set of parameters comprises the at least one status parameter.

4. The arrangement of claim 3, wherein the first computation module is further configured to compute, as a function of the measured data samples and the estimated data samples, a measured temporal change and an estimated temporal change in conductivity during the drain phase of the one or more fluid exchange cycles, and wherein the second computation module is operable to determine, by use of the parameter fitting algorithm, the respective candidate value to further minimize a difference between the measured temporal change and the estimated temporal change.

5. The arrangement of claim 3, wherein the set of parameters represents a diffusion capacity of one or more solutes through the peritoneal membrane and a filtration capacity of water through the peritoneal membrane.

6. The arrangement of claim 3, wherein the set of parameters further represents a tonicity of the individual.

7. The arrangement of claim 3, wherein the first computation module is configured to repeatedly compute the estimated data samples based on the respective candidate value of a set of parameter values determined by the second computation module, and the second computation module is configured to repeatedly determine the respective candidate value of the set of parameters based on the estimated data samples from the first computation module, wherein the second computation module is configured to output the at least one status parameter when a convergence criterion is fulfilled or a time limit is reached.

8. The arrangement of claim 1, wherein the first computation module is further configured to compute, based on the first data and by use of the mathematical model, a time sequence of estimated amounts of the treatment fluid in the peritoneal cavity for a time period during the one or more fluid exchange cycles.

9. The arrangement of claim 1, which is further configured to evaluate at least one status parameter for detection of a potential failure of the peritoneal membrane and, upon detection of the potential failure, generate an alarm or an alert.

10. The arrangement of claim 1, wherein the first computation module comprises a differential equation solver sub-module configured to calculate, from an initial time point to an end time point, an amount of the treatment fluid in the peritoneal cavity from the initial time point to the end time point including intermediate time steps, and to calculate the concentration of one or more solutes in the treatment fluid in the peritoneal cavity from the initial time point to the end time point including the intermediate time steps.

11. The arrangement of claim 1, wherein the one or more fluid exchange cycles comprises two consecutive exchange cycles, wherein the two or more time points comprise a time point during the drain phase of a first fluid exchange cycle, and a time point during the dwell phase of a second fluid exchange cycle following upon the first fluid exchange cycle.

12. The arrangement of claim 1, wherein the input is further arranged to receive fluid exchange data for the individual in a preceding time period before the one or more fluid exchange cycles, wherein the arrangement is further configured to estimate, based on the fluid exchange data, an initial concentration of one or more solutes in the treatment fluid in the peritoneal cavity at an evaluation starting point, and wherein the first computation module is configured to compute the estimated data samples based on the initial concentration.

13. The arrangement of claim 1, wherein the at least one status parameter comprises a volume of treatment fluid in the peritoneal cavity at a selected time point.

14. The arrangement of claim 13, wherein the measured data samples in the second data comprise a first data sample taken during a drain phase and a second data sample taken after completion of a fill phase subsequent to the drain phase, and wherein the second computation module is configured to determine the volume of treatment fluid in the peritoneal cavity at the selected time point.

15. The arrangement of claim 14, wherein the first and second data samples are taken during an initial probing cycle which comprises the drain phase and the fill phase and in which a restricted amount of the treatment fluid in the peritoneal cavity is extracted in the drain phase, the restricted amount corresponding to a fraction of a maximum fill volume of the peritoneal cavity.

16. The arrangement of claim 15, which is configured to provide output data representing the volume of treatment fluid in the peritoneal cavity, for receipt by a peritoneal dialysis arrangement that is operated to perform the peritoneal dialysis, such that the peritoneal dialysis arrangement is caused to initiate a drain phase after the initial probing cycle when the volume of the treatment fluid is above a limit value, and to initiate a fill phase after the initial probing cycle when the volume of treatment fluid is below the limit value.

17. The arrangement of claim 1, wherein the at least one status parameter comprises a tonicity parameter of the individual.

18. A peritoneal dialysis arrangement, comprising:

an extracorporeal fluid circuit that is connectable to a peritoneal access of an individual for conveying treatment fluid from/to a peritoneal cavity;

at least one sensor device, which is arranged in the extracorporeal fluid circuit and configured to provide data samples representative of a concentration of one or more solutes in the treatment fluid;

a control apparatus configured to operate the extracorporeal fluid circuit and obtain the data samples from the at least one sensor device; and an arrangement in accordance with claim 1, which is connected to receive the first and second data from the control apparatus.

19. A method of determining at least one status parameter of an individual undergoing peritoneal dialysis, the method comprising:

obtaining first data indicative of a flow rate as a function of time of a treatment fluid into and out of a peritoneal cavity, via a peritoneal cavity access of the individual, during one or more fluid exchange cycles, wherein each fluid exchange cycle includes a fill phase, a dwell phase, and a drain phase;

obtaining, from at least one sensor arranged in a fluid circuit and configured to provide data samples representative of a concentration of one or more solutes in the treatment fluid flowing through the fluid circuit, second data comprising measured data samples representing the concentration of the one or more solutes in the treatment fluid in the peritoneal cavity at two or more time points during the one or more fluid exchange cycles;

computing, based on the first data and by use of a mathematical model of a transport of water and solutes through a peritoneal membrane in the peritoneal cavity, estimated data samples representing the concentration of the one or more solutes in the treatment fluid in the peritoneal cavity at the two or more time points; and determining the at least one status parameter as a function of the measured data samples and the estimated data samples.

20. A non-transitory computer-readable medium comprising computer instructions which, when executed by one or more processors, cause the one or more processors to perform the method of claim 19.

* * * * *